United States Patent
Wenzel et al.

(10) Patent No.: US 9,743,994 B2
(45) Date of Patent: Aug. 29, 2017

(54) RIGHT ATRIUM INDICATOR

(71) Applicant: VASONOVA, INC., Palo Alto, CA (US)

(72) Inventors: Brian J. Wenzel, San Jose, CA (US); Kichang Lee, Newtwon, MA (US); Stephen P. Hanlon, San Ramon, CA (US); Miroslav Navratil, Jihlava (CZ); Jin Jiang, San Carlos, CA (US)

(73) Assignee: Vasonova, Inc., Palo Alto, CA (US)

( * ) Notice: Subject to any disclaimer, the term of this patent is extended or adjusted under 35 U.S.C. 154(b) by 0 days.

(21) Appl. No.: 15/132,242

(22) Filed: Apr. 19, 2016

(65) Prior Publication Data

US 2016/0256224 A1 Sep. 8, 2016

Related U.S. Application Data

(62) Division of application No. 13/829,522, filed on Mar. 14, 2013, now Pat. No. 9,345,447.

(Continued)

(51) Int. Cl.
*A61B 34/20* (2016.01)
*A61B 8/08* (2006.01)
(Continued)

(52) U.S. Cl.
CPC .............. *A61B 34/20* (2016.02); *A61B 5/026* (2013.01); *A61B 5/04012* (2013.01);
(Continued)

(58) Field of Classification Search
CPC ........... A61B 8/06; A61B 8/0841; A61B 8/12; A61B 8/488; A61B 5/061; A61B 5/04012;
(Continued)

(56) References Cited

U.S. PATENT DOCUMENTS 3,565,062 A 2/1971 Kuris et al.
4,143,650 A 3/1979 Hatke
(Continued)

FOREIGN PATENT DOCUMENTS

EP 0917069 A1 5/1999
EP 1181895 A2 2/2002
(Continued)

OTHER PUBLICATIONS

Benchimol et al.; Right atrium and superior vena cava flow velocity in man measured with the doppler-catheter flowmeter-telemetry system; The Amer. J of Med.; vol. 48; pp. 303-309; Mar. 1970.
(Continued)

*Primary Examiner* — Bo J Peng
(74) *Attorney, Agent, or Firm* — Baker & Hostetler LLP

(57) ABSTRACT

A method for determining the location of a medical device within a body is provided. The method includes transmitting from the medical device an acoustic signal; receiving with the medical device a reflected acoustic signal; advancing the medical device based on a first algorithm, the first algorithm including a first weighting factor and a first feature extracted from the reflected acoustic signal; determining a first location of the medical device based on the first algorithm; and moving the medical device to a second location based on a second algorithm, the second algorithm based on the determined first location and including at least one of a second weighting factor and a second feature extracted from the reflected acoustic signal. Also disclosed are systems and devices for performing the methods described herein.

7 Claims, 15 Drawing Sheets

Related U.S. Application Data

(60) Provisional application No. 61/643,888, filed on May 7, 2012, provisional application No. 61/643,890, filed on May 7, 2012, provisional application No. 61/649,172, filed on May 18, 2012, provisional application No. 61/649,196, filed on May 18, 2012.

(51) Int. Cl.
*A61B 5/06* (2006.01)
*A61B 8/12* (2006.01)
*A61B 5/04* (2006.01)
*A61B 5/0456* (2006.01)
*A61B 5/026* (2006.01)
*A61B 8/06* (2006.01)

(52) U.S. Cl.
CPC ............ *A61B 5/0456* (2013.01); *A61B 5/061* (2013.01); *A61B 5/065* (2013.01); *A61B 8/0841* (2013.01); *A61B 8/12* (2013.01); *A61B 8/488* (2013.01); *A61B 8/06* (2013.01); *A61B 2034/2063* (2016.02)

(58) Field of Classification Search
CPC ....... A61B 5/065; A61B 5/026; A61B 5/0456; A61B 34/20; A61B 2034/2063
See application file for complete search history.

(56) References Cited

U.S. PATENT DOCUMENTS

| | | |
|---|---|---|
| 4,324,258 A | 4/1982 | Huebscher et al. |
| 4,354,502 A | 10/1982 | Colley et al. |
| 4,503,861 A | 3/1985 | Entrekin |
| 4,549,879 A | 10/1985 | Groshong et al. |
| 4,637,401 A | 1/1987 | Johnston |
| 4,644,960 A | 2/1987 | Johans |
| 4,667,679 A | 5/1987 | Sahota |
| 4,692,148 A | 9/1987 | Kantrowitz et al. |
| 4,706,681 A | 11/1987 | Breyer et al. |
| 4,790,831 A | 12/1988 | Skribiski |
| 4,849,172 A | 7/1989 | Yafuso et al. |
| 4,856,529 A | 8/1989 | Segal |
| 4,896,677 A | 1/1990 | Kaneko et al. |
| 4,966,148 A | 10/1990 | Millar |
| 4,967,753 A | 11/1990 | Haase et al. |
| 4,979,510 A | 12/1990 | Franz et al. |
| 5,038,789 A | 8/1991 | Frazin |
| 5,046,497 A | 9/1991 | Millar |
| 5,047,930 A | 9/1991 | Martens et al. |
| 5,058,597 A | 10/1991 | Onoda et al. |
| 5,078,148 A | 1/1992 | Nassi et al. |
| 5,078,678 A | 1/1992 | Katims |
| 5,107,841 A | 4/1992 | Sturgill |
| 5,174,295 A | 12/1992 | Christian et al. |
| 5,190,045 A | 3/1993 | Frazin |
| 5,207,226 A | 5/1993 | Bailin et al. |
| 5,220,924 A | 6/1993 | Frazin |
| 5,269,289 A | 12/1993 | Takehana et al. |
| 5,271,404 A | 12/1993 | Corl et al. |
| 5,311,871 A | 5/1994 | Yock |
| 5,431,628 A | 7/1995 | Millar |
| 5,477,858 A | 12/1995 | Norris et al. |
| 5,492,125 A | 2/1996 | Kim et al. |
| 5,546,949 A | 8/1996 | Frazin et al. |
| 5,566,674 A | 10/1996 | Weng |
| 5,575,286 A | 11/1996 | Weng et al. |
| 5,588,432 A | 12/1996 | Crowley |
| 5,640,961 A | 6/1997 | Verdonk |
| 5,657,760 A | 8/1997 | Ying et al. |
| 5,666,958 A | 9/1997 | Rothenberg et al. |
| 5,669,389 A | 9/1997 | Rotteveel et al. |
| 5,693,032 A | 12/1997 | Bierman |
| 5,697,377 A | 12/1997 | Wittkampf |
| 5,722,959 A | 3/1998 | Bierman |
| 5,733,323 A | 3/1998 | Buck et al. |
| 5,749,364 A | 5/1998 | Sliwa, Jr. et al. |
| 5,782,766 A | 7/1998 | Weng et al. |
| 5,785,657 A | 7/1998 | Breyer et al. |
| 5,795,298 A | 8/1998 | Vesely et al. |
| 5,803,083 A | 9/1998 | Buck et al. |
| 5,857,973 A | 1/1999 | Ma et al. |
| 5,860,951 A | 1/1999 | Eggers et al. |
| 5,876,342 A | 3/1999 | Chen et al. |
| 5,878,746 A | 3/1999 | Lemelson et al. |
| 5,891,036 A | 4/1999 | Izumi |
| 5,897,488 A | 4/1999 | Ueda |
| 5,908,385 A | 6/1999 | Chechelski et al. |
| 5,935,143 A | 8/1999 | Hood |
| 5,938,603 A | 8/1999 | Ponzi |
| 5,999,846 A | 12/1999 | Pardey et al. |
| 6,007,491 A | 12/1999 | Ling et al. |
| 6,059,731 A | 5/2000 | Seward et al. |
| 6,083,170 A | 7/2000 | Ben-Haim |
| 6,120,445 A | 9/2000 | Grunwald |
| 6,179,781 B1 | 1/2001 | Phillips |
| 6,179,782 B1 | 1/2001 | Cuce |
| 6,213,947 B1 | 4/2001 | Phillips |
| 6,251,073 B1 | 6/2001 | Imran et al. |
| 6,264,611 B1 | 7/2001 | Ishikawa et al. |
| 6,364,838 B1 | 4/2002 | Freiburger et al. |
| 6,500,130 B2 | 12/2002 | Kinsella et al. |
| 6,520,916 B1 | 2/2003 | Brennen |
| 6,542,626 B1 | 4/2003 | Brouwer et al. |
| 6,551,244 B1 | 4/2003 | Gee |
| 6,556,695 B1 | 4/2003 | Packer et al. |
| 6,561,979 B1 | 5/2003 | Wood et al. |
| 6,591,144 B2 | 7/2003 | Pigott |
| 6,594,524 B2 | 7/2003 | Esteller et al. |
| 6,612,992 B1 | 9/2003 | Hossack et al. |
| 6,638,243 B2 | 10/2003 | Kupiecki |
| 6,685,648 B2 | 2/2004 | Flaherty et al. |
| 6,689,119 B1 | 2/2004 | Di Caprio et al. |
| 6,695,785 B2 | 2/2004 | Brisken et al. |
| 6,704,590 B2 | 3/2004 | Haldeman |
| 6,719,756 B1 | 4/2004 | Muntermann |
| 6,733,454 B1 | 5/2004 | Bakircioglu et al. |
| 6,740,590 B1 | 5/2004 | Yano et al. |
| 6,749,606 B2 | 6/2004 | Keast et al. |
| 6,814,702 B2 | 11/2004 | Redano |
| 6,842,639 B1 | 1/2005 | Winston et al. |
| 6,866,677 B2 | 3/2005 | Douk et al. |
| 6,896,658 B2 | 5/2005 | Ji et al. |
| 6,931,269 B2 | 8/2005 | Terry |
| 6,973,352 B1 | 12/2005 | Tsutsui et al. |
| 7,037,290 B2 | 5/2006 | Gardeski et al. |
| 7,043,293 B1 | 5/2006 | Baura |
| 7,150,716 B2 | 12/2006 | Jones et al. |
| 7,200,435 B2 | 4/2007 | Ricci et al. |
| 7,204,798 B2 | 4/2007 | Zdeblick et al. |
| 7,225,013 B2 | 5/2007 | Geva et al. |
| 7,302,285 B2 | 11/2007 | Fuimaono et al. |
| 7,346,393 B2 | 3/2008 | Spinelli et al. |
| 7,367,949 B2 | 5/2008 | Korhonen et al. |
| 7,393,501 B2 | 7/2008 | Zumeris et al. |
| 7,422,563 B2 | 9/2008 | Roschak et al. |
| 7,433,853 B2 | 10/2008 | Brockway et al. |
| 7,485,095 B2 | 2/2009 | Shusterman |
| 7,599,730 B2 | 10/2009 | Hunter et al. |
| 7,627,386 B2 | 12/2009 | Mo et al. |
| 7,640,055 B2 | 12/2009 | Geva et al. |
| 7,668,579 B2 | 2/2010 | Lynn |
| 7,697,972 B2 | 4/2010 | Verard et al. |
| 7,708,696 B2 | 5/2010 | Ritter et al. |
| 7,733,224 B2 | 6/2010 | Tran |
| 7,794,407 B2 | 9/2010 | Rothenberg |
| 7,833,221 B2 | 11/2010 | Voegele et al. |
| 7,966,061 B2 | 6/2011 | Al-Abed et al. |
| 7,981,038 B2 | 7/2011 | Kanade et al. |
| 7,991,458 B2 | 8/2011 | Hardahl et al. |
| 8,046,052 B2 | 10/2011 | Verard et al. |
| 8,052,648 B2 | 11/2011 | Dikeman et al. |
| 8,060,185 B2 | 11/2011 | Hunter et al. |
| 8,409,103 B2 | 4/2013 | Grunwald et al. |

(56) References Cited

U.S. PATENT DOCUMENTS

| | | | |
|---|---|---|---|
| 8,636,659 B2 | 1/2014 | Alpert et al. |
| 2002/0045810 A1 | 4/2002 | Ben-Haim |
| 2002/0087156 A1 | 7/2002 | Maguire et al. |
| 2002/0111548 A1 | 8/2002 | Swanson et al. |
| 2002/0151790 A1 | 10/2002 | Abend |
| 2002/0156363 A1 | 10/2002 | Hunter et al. |
| 2002/0168618 A1 | 11/2002 | Anderson et al. |
| 2002/0188257 A1 | 12/2002 | Bierman |
| 2003/0083717 A1 | 5/2003 | Mlynski et al. |
| 2003/0109785 A1 | 6/2003 | Buck et al. |
| 2003/0191392 A1 | 10/2003 | Haldeman |
| 2004/0011358 A1 | 1/2004 | Smaldone et al. |
| 2004/0039436 A1 | 2/2004 | Spenser et al. |
| 2004/0102719 A1 | 5/2004 | Keith et al. |
| 2004/0116809 A1 | 6/2004 | Chow et al. |
| 2004/0116969 A1 | 6/2004 | Owen et al. |
| 2004/0158143 A1 | 8/2004 | Flaherty et al. |
| 2004/0254523 A1 | 12/2004 | Fitzgerald et al. |
| 2005/0085718 A1 | 4/2005 | Shahidi |
| 2005/0148836 A1 | 7/2005 | Kleen et al. |
| 2005/0159738 A1 | 7/2005 | Visram et al. |
| 2006/0079868 A1 | 4/2006 | Makin et al. |
| 2006/0084883 A1 | 4/2006 | Linker |
| 2006/0094923 A1 | 5/2006 | Mate |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0167738 A1 | 7/2007 | Timinger et al. |
| 2007/0265526 A1 | 11/2007 | Govari et al. |
| 2007/0276334 A1 | 11/2007 | Bierman et al. |
| 2007/0299352 A1 | 12/2007 | Harlev et al. |
| 2008/0058607 A1 | 3/2008 | Watrous |
| 2008/0161669 A1 | 7/2008 | Hauck et al. |
| 2008/0188740 A1 | 8/2008 | Diaz et al. |
| 2009/0005675 A1 | 1/2009 | Grunwald et al. |
| 2009/0043216 A1 | 2/2009 | Lin et al. |
| 2009/0118612 A1 | 5/2009 | Grunwald et al. |
| 2009/0143740 A1 | 6/2009 | Bierman et al. |
| 2009/0156926 A1 | 6/2009 | Messerly et al. |
| 2009/0177090 A1 | 7/2009 | Grunwald et al. |
| 2009/0182283 A1 | 7/2009 | Sloan |
| 2009/0234328 A1 | 9/2009 | Cox et al. |
| 2009/0259124 A1 | 10/2009 | Rothenberg |
| 2009/0262977 A1 | 10/2009 | Huang et al. |
| 2009/0287070 A1 | 11/2009 | Baker, Jr. |
| 2009/0287191 A1 | 11/2009 | Ferren et al. |
| 2010/0036227 A1 | 2/2010 | Cox et al. |
| 2010/0204569 A1 | 8/2010 | Burnside et al. |
| 2011/0087114 A1 | 4/2011 | Moulder |
| 2011/0196248 A1 | 8/2011 | Grunwald |
| 2011/0257600 A1 | 10/2011 | Kessler |
| 2011/0282187 A1 | 11/2011 | Harlev et al. |
| 2011/0317006 A1 | 12/2011 | Kuboyama et al. |
| 2012/0035434 A1 | 2/2012 | Ferren et al. |
| 2012/0083702 A1 | 4/2012 | Ingold, Jr. et al. |
| 2012/0136242 A1 | 5/2012 | Qi et al. |

FOREIGN PATENT DOCUMENTS

| | | | |
|---|---|---|---|
| JP | 62500703 A | 3/1987 |
| JP | 62236532 A | 10/1987 |
| JP | 08229044 A | 9/1996 |
| JP | 09253084 A | 9/1997 |
| JP | 10277039 A | 10/1998 |
| JP | 2004500210 A | 1/2004 |
| JP | 2004130114 A | 4/2004 |
| JP | 2006513731 A | 4/2006 |
| JP | 2008541799 A | 11/2008 |
| JP | 2010532227 A | 10/2010 |
| WO | WO9808440 | 3/1998 |
| WO | WO0170303 | 9/2001 |
| WO | WO2006051523 A2 | 5/2006 |
| WO | WO2006122001 A2 | 11/2006 |
| WO | WO2007047360 A2 | 4/2007 |
| WO | WO2009003138 A1 | 12/2008 |
| WO | WO2012064769 A2 | 5/2012 |

OTHER PUBLICATIONS

Benchimol et al.; Bidirectional blood flow velocity in the cardiac chambers and great vessels studied with the doppler ultrasonic flowmeter; The Amer. J of Med.; vol. 52; pp. 467-473; Apr. 1972.

Bowers et al.; Respiratory rate derived from principal component analysis of single lead electrocardiogram; Conference Proc.; Computers in Cardiology; Bologna, IT; 2008; vol. 35; pp. 437-440; Sep. 14-17, 2008.

Bidoggia et al.; Transseptal left heart catheterization: usefulness of the intracavitary electrocardiogram in the localization of the fossa ovalis; Catheterization and Cardiovascular Diagnosis; New York, NY; vol. 24; No. 3; pp. 221-225; Nov. 1, 1991.

Bossert et al.; Swan-Ganz catheter-induced severe complications in cardiac surgery: right ventricular perforation, knotting, and rupture of a pulmonary artery; J. Car. Surg.; vol. 21; No. 3; pp. 292-295; May/Jun. 2006.

Brunner, Eberhard; Ultrasound system considerations and their impact on front-end components; Analog Devices, Inc.; pp. 1-19; May-Jun. 2002.

Fearon et al.; Evaluating intermediate coronary lesions in the cardiac catheterization laboratory; Rev Cardiovasc Med; vol. 4; No. 1; pp. 1-7; Winter 2003.

Hellerstein et al.; Recording of intracavity potentials through a single lumen, saline filled cardiac catheter; P.S.E.B.M.,; vol. 71; pp. 58-60; Apr. 5, 1949.

Kalmanson et al.; Letter to the Editor; "Directional vs bidirectional doppler velocimeter"; Am. Heart J.; vol. 83; No. 3; pp. 437; Mar. 1972.

Lewis et al.; A Study of Normal and abnormal femoral venous flow velocity using a directional doppler; Br. J. Surg: vol. 59, No. 4; pp. 303; Apr. 1972.

McGee, et al.; Accurate placement of central venous catheters: A prospecitve, randomized, multicenter trial; Critical Care Medicine, vol. 21, No. 8, pp. 1118-1123, Aug. 1993.

Naylor; Reduction of malposition in peripherally inserted central catheters with tip location system; JAVA; vol. 12; No. 1; pp. 29-31; Spring 2007.

Pittiruti et al.; The EKG method for positioning the tip of PICCs; results from two preliminary studies;JAVA; vol. 13; No. 1; pp. 112-119; Winter 2008.

Radke et al.; Control of the placement of a central venous catheter using doppler ultrasound; Der Anaesthesist May 1990; vol. 39; No. 5; pp. 283-287; May 1990.

Starr, et al.; EKG guided placement of subclavian CVP Catheters using J-wire; Ann. Surg.; vol. 204, No. 6, pp. 573-676, Dec. 1986.

Stas et al.; Peroperative intranasal electrographic control of catheter tip position in access ports placed by venous cut-down technique;EJSO; vol. 27; pp. 316-320; Apr. 2001.

Schummer et al.; Central venous catheters-the inability of 'intra-atrial ECG' to prove adequate positioning; British Jour. of Anaesthesia, vol. 93, No. 2; pp. 193-198, Jun. 25, 2004.

Grunwald et al.; U.S. Appl. No. 13/844,408 entitled "Apparatus and method for endovascular device guiding and positioning using physiological parameters," filed Mar. 15, 2013.

Lee et al.; U.S. Appl. No. 13/829,650 entitled "Systems and methods for detection of the superior vena cava area and the cavoatrial junction," filed Mar. 14, 2013.

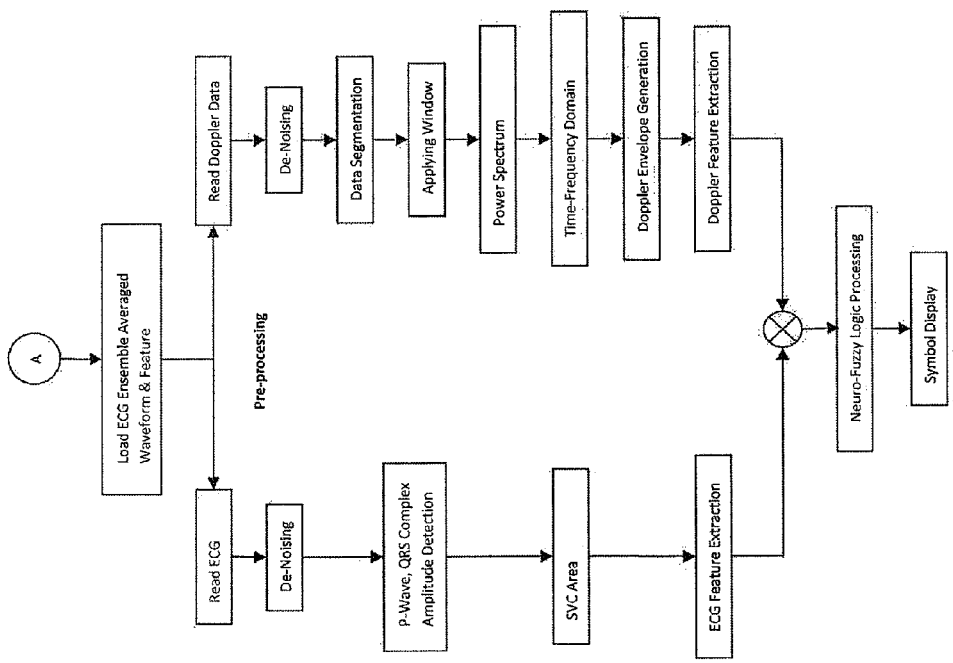
Figure 8 Flow charts of the pre-processing and processing of the ECG and Doppler data to obtain the output results.

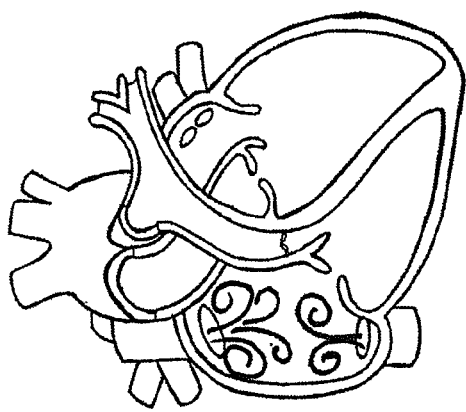
Figure 9A. Turbulent blood flow formation at CAJ.

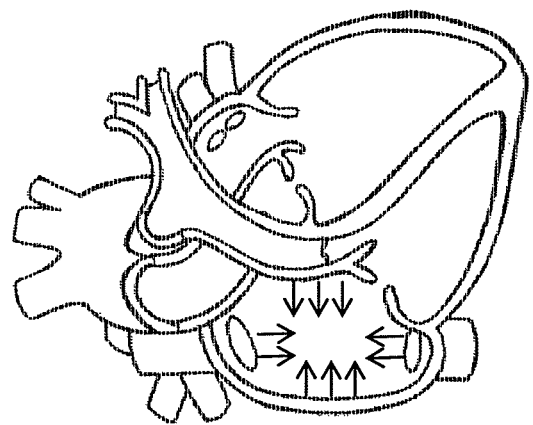
Figure 9B. Turbulent blood flow formation at RA.

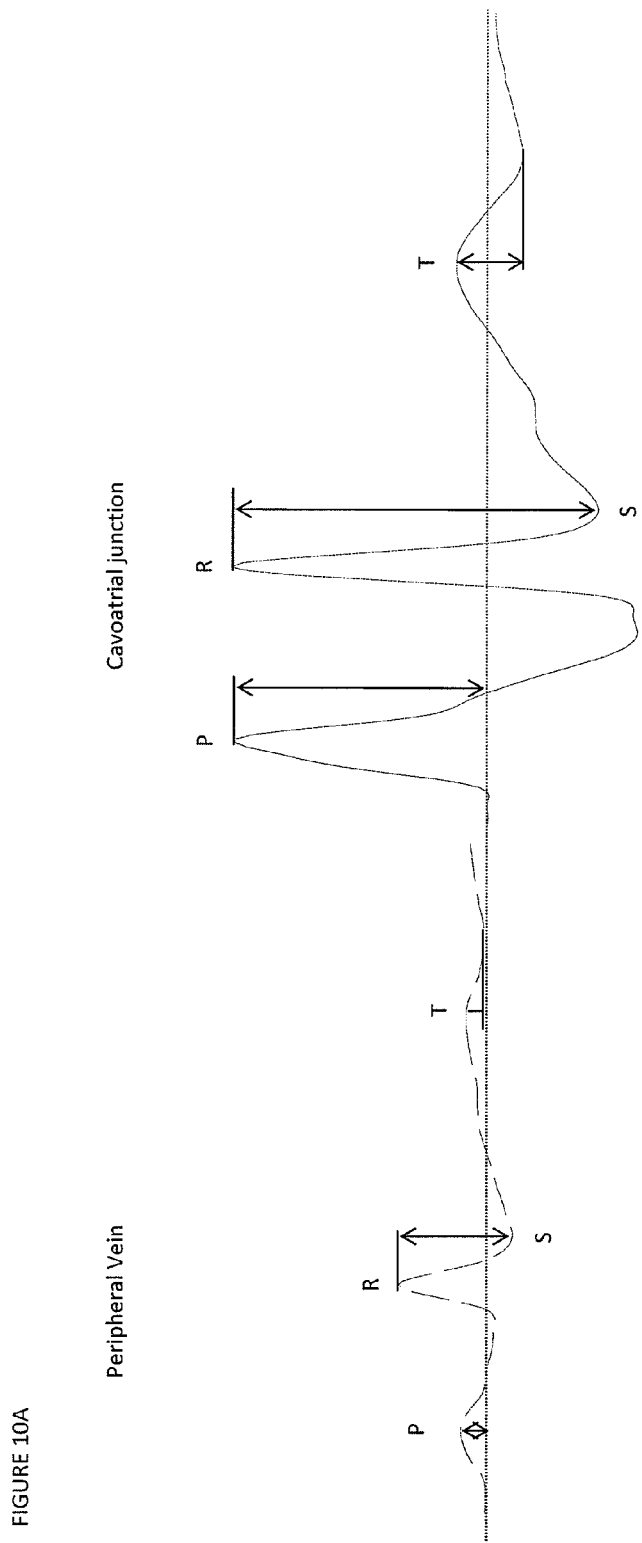

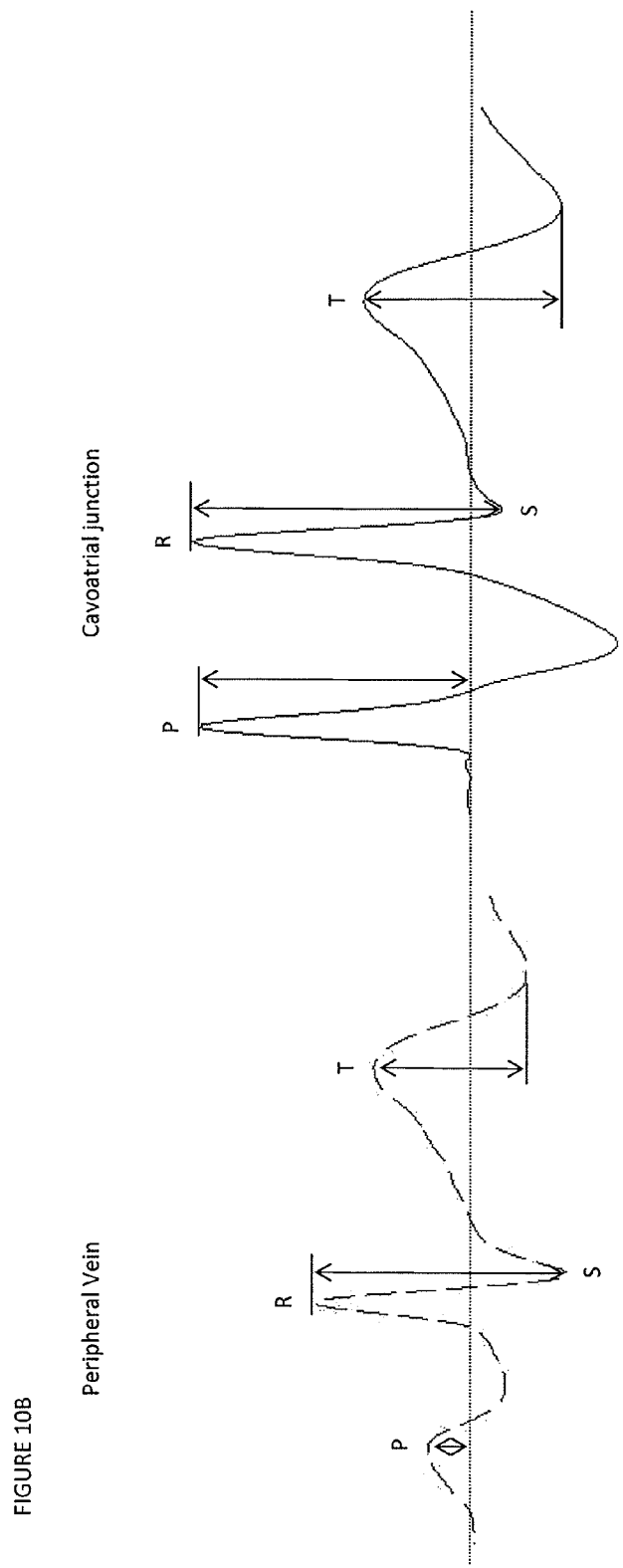

RIGHT ATRIUM INDICATOR

CROSS REFERENCE TO RELATED APPLICATIONS

This application is a divisional of U.S. patent application Ser. No. 13/829,522, filed Mar. 14, 2013, which claims priority to U.S. Provisional Patent App. No. 61/643,888, filed May 7, 2012, U.S. Provisional Patent App. No. 61/643,890, filed May 7, 2012, U.S. Provisional Patent App. No. 61/649,172, filed May 18, 2012, and U.S. Provisional Patent App. No. 61/649,196, filed May 18, 2012, each of which is hereby incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate, in general, to an endovascular navigation system and methods for guiding and positioning an endovascular device using an algorithm-based artificial intelligence processor.

BACKGROUND

This invention provides a method to substantially increase the accuracy and reduce the need for imaging related to placing an intravascular catheter or other device. Aspects of the invention relate to the guidance, positioning and placement confirmation of intravascular devices, such as catheters, stylets, guidewires and other elongate bodies that are typically inserted percutaneously into the venous vasculature, including flexible elongate bodies. Currently, these goals are suboptimally achieved using x-ray imaging, fluoroscopy, and in some cases ultrasound imaging. ECG alone is used but has severe limitations with accuracy, navigation along the entire venous pathway, and is of minimal value in the presence of arrhythmia or abnormal heart cardiac activity. Reduced imaging can reduce the amount of radiation that patients are subjected to, reduce the time required for the procedure, and decrease the cost of the procedure by reducing the time needed in the radiology department. The degree of accuracy provided by the invention is critical because there are patient consequences to an intravascular catheter in a location that is not precisely correct.

The vasculature of mammals has long been accessed to provide therapy, administer pharmacological agents, and meet other clinical needs. Numerous procedures exist in both venous and arterial systems and are selected based on patient need. One challenge common to all vascular-based therapies is health care provider access to the specific location or section of the vascular tree.

One common venous access procedure is central venous access. Central venous access is the placement of a venous catheter in a vein that leads directly to the heart. Central venous catheters (CVCs) are ubiquitous in modern hospital and ambulatory medicine, with up to 8 million insertions per year in the U.S. and a similar number outside the U.S.

Venous access devices are most often used for the following purposes:

Administration of medications, such as antibiotics, chemotherapy drugs, and other IV drugs Administration of fluids and nutritional compounds (hyperalimentation)

Transfusion of blood products

Hemodialysis

Multiple blood draws for diagnostic testing

Consequences of catheter tip placement inaccuracies include, among other things:

Increased risk of thrombus formation

Venous damage due to drug toxicity

Increased risk of infection

Additional radiation exposure

Central venous access devices are typically small, flexible tubes placed in large veins for people who require frequent access to their bloodstream. The devices typically remain in place for long periods: week, months, or even longer.

Central venous access devices are usually inserted in one of three ways:

a) Directly: Catheters are inserted by tunneling under the skin into either the subclavian vein (located beneath the collarbone) or into the internal jugular vein (located in the neck). The part of the catheter where medications are administered or blood is drawn remains outside of the skin.

b) Through a port: Unlike catheters, which exit from the skin, a port is placed completely under the skin. With a port, a raised disk about the size of a quarter or half dollar is felt underneath the skin. Blood is drawn or medication is delivered by placing a tiny needle through a subcutaneous injection port.

c) Indirectly via a peripheral vein: Peripherally inserted central catheter (PICC) lines, unlike central catheters and ports, are not inserted directly into the central vein. A PICC line is inserted into a large vein in the upper arm and advanced forward into the larger subclavian vein.

CVCs and ports are usually inserted by a surgeon or surgical assistant in a surgical suite. A PICC line can be put in at bedside, usually by a specially-trained nurse. In this latter case, confirmation by X-ray is currently required for assessing the success of the PICC placement. Therefore PICC procedures as currently practiced involve exposure to X-ray, and manipulation of the catheter may increase the risks of infection.

Traditional, surgically-placed central catheters are increasingly being replaced by peripherally inserted central venous access devices. PICC lines usually cause fewer severe complications than central venous access devices. The PICC line placement procedure has been used to deliver long-term drug delivery, chemotherapy procedures, delivery of intravenous medications or intravenous nutrition (hyperalimentation) and taking blood samples. Insertion of PICC lines is a routine procedure in that it is carried out for a variety of treatments, and more than once in the same patient when the catheter is to be left in place for any length of time. Even though it is routine, it is a very time and labor-intensive procedure for the hospital staff, which also makes it expensive. During the procedure the physician or nurse places the catheter into a superficial upper arm vein such as the basilic, brachial, or cephalic with the goal of having the distal end of the catheter reach the superior vena cava (SVC). After entering the superficial vein at ⅓ and ⅔ of the upper arm, the catheter is advanced up the subclavian vein, then the brachiocephalic vein and finally it enters the SVC. One caveat is to make sure that the PICC line does not enter and remain in the undesired veins such as jugular, azygos, or other vein.

In addition to guiding the catheter through the vasculature, the final location of the catheter tip is very important to the success of the procedure. Catheters will generally function equally well for pressure measurement and fluid infusion if the tip is situated in a major vein, above the heart (i.e., SVC), or below the heart (i.e., inferior vena cava; IVC). For dialysis or the infusion of irritant/hypertonic fluids, a high rate of blood flow past the catheter tip is desirable and this requires the placement of the luminal opening in as large a vessel as possible. However, CVC/PICC instructions for use give strong warnings about the requirement for catheter tips to lie outside the heart to avoid perforation and subsequent pericardial tamponade. Likewise positioning the catheter tip away from small peripheral veins is important to avoid damaging the vein wall or occluding the vein due the caustic effects of the infusing solution. An interventional radiologist may use a fluoroscopic agent to delineate the veins in the body and subsequently verify the correct positioning of the catheter tip using a post-operative X-ray. Currently, a post-operative X-ray is performed routinely while some studies have shown that only 1.5% of the cases are subject to complications that would indeed require X-ray imaging.

Current methods for guiding PICC lines include the legacy landmark measurement technique, X-ray guidance, external electromagnetic sensors, and intravascular sensors (e.g. ECG sensor). In the case of external electromagnetic sensors, the endovascular device is guided by assessing the distance between an electromagnetic element at the tip of the device (e.g. a coil) and an external (out of body) receiver. This method is inaccurate because it does not actually indicate location in the vascular but instead indicates only relative position to an external reference. In the case of ECG-guided catheters, the classic increase in P-wave size, known as 'P-atriale", is a widely accepted criterion for determining location of CVC/PICC tips in the proximity of the sino-atrial node. Current methods include using a catheter filled with saline and an ECG adaptor at the proximal end connected to an ECG system. This method is inaccurate because it does not indicate location in the blood vessel but instead indicates the proximity of the sino-atrial node (SA node).

Because of known inaccuracies, all the current methods in use explicitly require the use of a confirmatory chest X-ray to verify and confirm location of the tip of the endovascular device at the desired target in the vasculature.

Additional approaches based on the use of non-imaging ultrasound are described in U.S. Patent Pub. Nos. 2007/0016068, 2007/0016069, 2007/0016070, and 2007/0016072, incorporated herein for all purposes. Limitations of an approach based exclusively on measuring right-atrial electrocardiograms have been described in the literature, for example, in [1]: W. Schummer et al., CVCs—the inability of 'intra-atrial ECG' to prove adequate positioning, British Journal of Anaesthesia, 93 (2): 193-8, 2004.

What is needed is a guidance system and method that overcome the above and other disadvantages of known systems and methods.

In view of the variable nature of physiological signal information used during endovascular positioning and guidance, what is needed are methods and apparatuses to optimize the use of physiological signal information and take into account the variable accuracy and usefulness of the signal information.

What is needed is a guidance system and method that can accurately position a device in irregular cardio-vascular environments such as the vasculature of patients with an aneurysm or arrhythmia.

What is needed is increased accuracy of the catheter tip placement without additional X-rays and manipulation of the catheter.

SUMMARY OF THE DISCLOSURE

The present invention relates to an endovascular navigation system and methods for guiding and positioning an endovascular device using an algorithm-based artificial intelligence processor.

In some embodiments, a method for determining the location of a medical device within a body is provided. The method includes transmitting from the medical device an acoustic signal; receiving with the medical device a reflected acoustic signal; advancing the medical device based on a first algorithm, the first algorithm including a first weighting factor and a first feature extracted from the reflected acoustic signal; determining a first location of the medical device based on the first algorithm; and moving the medical device to a second location based on a second algorithm, the second algorithm based on the determined first location and including at least one of a second weighting factor and a second feature extracted from the reflected acoustic signal.

In some embodiments, the method further includes detecting an ECG signal, wherein the first algorithm includes a third feature extracted from the ECG signal.

In some embodiments, the third feature is the R-wave of the ECG signal.

In some embodiments, a method for detecting that a medical device has entered the right atrium of a patient is provided. The method includes transmitting from the medical device an acoustic signal; receiving with the medical device a reflected acoustic signal; extracting one or more features indicative of turbulent flow from the acoustic signal; determining a turbulent flow pattern based on the extracted one or more features; and determining whether the medical device has entered the right atrium based on the determined turbulent flow pattern.

In some embodiments, the one or more features include a frequency content of the acoustic signal over time.

In some embodiments, the method further includes indicating that the medical device has entered the right atrium when the frequency content of the acoustic signal over time changes between antegrade dominant and retrograde dominant while the medical device is not being advanced or retracted.

In some embodiments, the one or more features includes an antegrade power signal, a retrograde power signal, and a ratio of the antegrade power signal to the retrograde power signal.

In some embodiments, the method further includes indicating that the medical device has entered the right atrium when an average value of the ratio of the antegrade power signal to the retrograde power signal over a cardiac cycle is close to one.

In some embodiments, the one or more features includes an overall power of the acoustic signal.

In some embodiments, the method further includes generating a Mel-frequency cepstrum of the acoustic signal; and determining one or more coefficients of the Mel-frequency cepstrum.

In some embodiments, the method further includes comparing the determined one or more coefficients with a database of coefficients based on turbulent and non-turbulent blood flow.

In some embodiments, the method further includes monitoring respiration and removing respiratory artifacts from the acoustic signal.

In some embodiments, a method for guiding a medical device to a target location within a patient's cardiovascular system is provided. The method includes transmitting from the medical device an acoustic signal; receiving with the medical device a reflected acoustic signal; extracting one or more features indicative of blood flow characteristics from the acoustic signal; determining a plurality of scores for a plurality of membership functions, each membership function comprising a series of extracted features, each extracted feature modified by a weighting factor, wherein the plurality of membership functions include at least one membership function for the target location within the cardiovascular system, at least one membership function for moving the device within the cardiovascular system, and at least one membership function for a secondary location within the cardiovascular system; and changing at least one weighting factor or at least one extracted feature in the series of extracted features of at least one membership function when the score of the membership function for the secondary location within the cardiovascular system is the greatest score.

In some embodiments, the target location is the SVC.

In some embodiments, the secondary location is the right atrium.

In some embodiments, a system for determining the location of a medical device within a body is provided. The system includes an elongate body having an non-imaging ultrasound transducer disposed on a distal portion of the elongate body; a processor configured to receive and process a reflected acoustic signal from the non-imaging ultrasound transducer; and memory for storing instructions, which when executed by the processor, causes the processor to: provide instructions to advance the elongate body based on a first algorithm, the first algorithm including a first weighting factor and a first feature extracted from the reflected acoustic signal; determine a first location of the elongate body based on the first algorithm; and provide instructions to move the elongate body to a second location based on a second algorithm, the second algorithm based on the determined first location and including at least one of a second weighting factor and a second feature extracted from the reflected acoustic signal.

In some embodiments, a system for detecting that a medical device has entered the right atrium of a patient is provided. The system includes an elongate body having an non-imaging ultrasound transducer disposed on a distal portion of the elongate body; a processor configured to receive and process a reflected acoustic signal from the non-imaging ultrasound transducer; and memory for storing instructions, which when executed by the processor, causes the processor to: extract one or more features indicative of turbulent flow from the reflected acoustic signal; determine a turbulent flow pattern based on the extracted one or more features; and determine whether the elongate body has entered the right atrium based on the determined turbulent flow pattern.

In some embodiments, the one or more features includes a frequency content of the reflected acoustic signal over time.

In some embodiments, the memory further comprises instructions, which when executed by the processor, causes the processor to indicate that the elongate body has entered the right atrium when the frequency content of the acoustic signal over time changes between antegrade dominant and retrograde dominant while the elongate body is not being advanced or retracted.

In some embodiments, the one or more features includes an antegrade power signal, a retrograde power signal, and a ratio of the antegrade power signal to the retrograde power signal.

In some embodiments, the memory further comprises instructions, which when executed by the processor, causes the processor to indicate that the elongate body has entered the right atrium when an average value of the ratio of the antegrade power signal to the retrograde power signal over a cardiac cycle is close to one.

In some embodiments, the one or more features includes an overall power of the reflected acoustic signal.

In some embodiments, the memory further comprises instructions, which when executed by the processor, causes the processor to generate a Mel-frequency cepstrum of the reflected acoustic signal; and determine one or more coefficients of the Mel-frequency cepstrum.

In some embodiments, the memory further comprises instructions, which when executed by the processor, causes the processor to compare the determined one or more coefficients with a database of coefficients based on turbulent and non-turbulent blood flow.

In some embodiments, the memory further comprises instructions, which when executed by the processor, causes the processor to remove respiratory artifacts from the acoustic signal.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 8 shows a flow chart of an embodiment of the pre-processing and processing of the ECG and Doppler data;

FIGS. 9A and 9B illustrate turbulent blood flow formation at the CAJ and RA from the intermixing of blood from the IVC and SVC and the movement of the walls of the RA;

FIGS. 10A and 10B illustrate the ECG waveform of two exemplary patients; and

DETAILED DESCRIPTION

Figure 1:
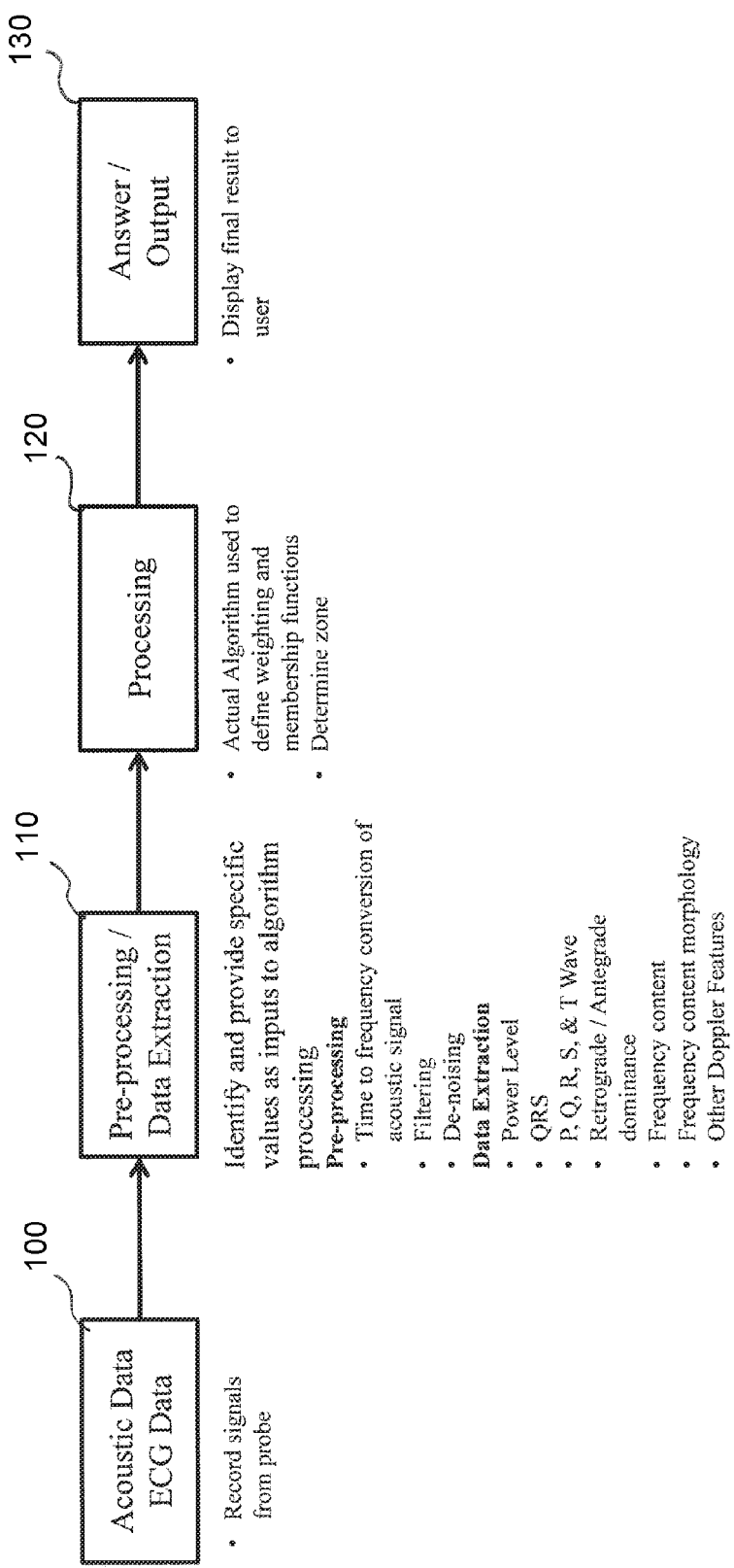
FIG. 1 is a flow chart of one embodiment of the data acquisition and processing procedure used to navigate a device within the vasculature of a patient.

An aspect of the invention includes an endovenous access and guidance system enabled with artificial intelligence capabilities. The system includes a transducer and an electric sensor on a distal end of an endovascular instrument, such as a catheter for example, a control system connected to the transducer and electric sensor, the control system being configured to generate and receive at least one acoustic signal using the transducer and receive at least one electrical signal, a pre-processor containing computer-readable instructions for manipulating the acoustic and electrical signal inputs to extract information related to one or more desired parameters, a processor configured to evaluate the acoustic and electrical features to generate an output related to guidance of the instrument, and an output device for displaying an indication of the output generated by the processor. In some embodiments, the system can include memory for storing the computer readable instruction. In some embodiments, the computer readable instructions can be implemented in an application specific integrated circuit (ASIC). The transducer can be an acoustic transducer, such as an ultrasound transducer. The electric sensor can be an sensor that detects the electrical signals generated by the heart, such as an ECG sensor. The processor may evaluate the information using artificial intelligence and inference rules, comparisons to information in a database, probabilities, among others. The system may use an electrical signal measured by an electric sensor as a confirmation input. The electrical signal can be an ECG signal or a portion of an ECG signal, such as the P-wave, QRS complex, or other features of the ECG signal. Further disclosed is a method of navigating and positioning an endovascular device in a vasculature, and more specifically, in a blood vessel.

In a previous version of the algorithm as described in U.S. application Ser. No. 13/292,010, filed on Nov. 8, 2011, entitled "Endovascular Navigation System and Method" which is hereby incorporated by reference in its entirety, there were 4 status indicators: Green (State 1), Blue (State 2), Red (State 3), and Yellow (State 0). These four indicators would guide the user to go straight or continue advancing the device (State 1), indicate that the device was at the target location (State 2), withdraw or retract the device (State 3), and wait (State 0), respectively. However, these indicators only give specific location guidance with respect to the cavo-atrial junction (CAJ) and the "Blue" target location indicator. Otherwise, the user has little indication (or information) of where the tip of the catheter may reside. By providing the user with additional information about the tip location, the user will have greater confidence in their ability to find the CAJ point and to avoid potentially unfavorable situations (e.g., catheter in the heart). Additionally, the location of the catheter tip may provide a gating function for the processor such as changing the weights, parameters, features and formulas of the algorithms based on the current location of the catheter tip to increase the accuracy of the placing the catheter tip in the ideal or desired location.

For example, one of the locations of interest is the right atrium. The presence of a catheter tip in the right atrium may cause an arrhythmia and cardiac tamponade. Therefore, it would be desirable in some embodiments to either avoid or prevent unintentional insertion into the right atrium or quickly remove the catheter tip from the right atrium after unintentional insertion into the right atrium. The current algorithm may detect the right atrium as a Status 3 Zone (Red) if the retrograde acoustic signal is stronger than the antegrade acoustic signal, where antegrade flow in the blood vessel, indicated by an antegrade acoustic signal, is flow away from the transducer and/or sensor. Retrograde flow in the blood vessel, indicated by a retrograde acoustic signal, is flow toward the transducer and/or sensor. However, the flow pattern of the right atrium is not purely antegrade like the brachiocephalic vein or purely retrograde like the internal jugular vein. The right atrium has a distinct flow pattern caused by three occurrences:

(1) the SVC (an antegrade flow pattern) connects to the IVC (a retrograde flow pattern), (2) the chamber of the right atrium is larger than either the SVC or the IVC, and (3) the right atrial wall moves with each atrial contraction.

These three occurrences, as illustrated in FIGS. 9A and 9B, create a multi-directional blood flow pattern and/or turbulent flow pattern caused by the mixing of blood from the SVC and IVC, as well as the movement of the atrial wall. This turbulent flow pattern is dependent on the location within the right atrium as well. The turbulent flow pattern near:

(1) the SVC will be antegrade dominant;

(2) the IVC will be retrograde dominant;

(3) during diastole the blood flow through tricuspid valve will be antegrade dominant and highly pulsatile with each ventricular contraction.

During the general case of catheter insertion into a vein, the blood flow by the transducer will be antegrade dominant as the blood travels to the heart. As the catheter tip approaches the heart, the blood flow volume increases as a result of the merging of several branch vessels and larger vessel diameters that are closer to the heart. The increased flow volume leads to a larger antegrade signal. If the catheter enters the right atrium, the blood flow pattern will change from antegrade dominant to turbulent flow.

In addition to the blood flow pattern analysis in U.S. application Ser. No. 13/292,010 referenced above, an additional analysis will be performed to determine the presence of turbulent blood flow. The pre-processor will extract useful features from the acoustic signal indicative of turbulent flow. There are several possible features that could be used to determine the flow pattern, as further described below and in FIGS. 1 and 2. One of the possible features is the frequency content of the antegrade acoustic and retrograde acoustic signal and the changes in the frequency content over time. The frequency content of the non-imaging acoustic Doppler signal represents the blood flow velocity. Essentially, the higher the frequency component of the acoustic signal, the higher the blood velocity. In some embodiments, the frequency content of the acoustic signal between about 5 and 15 kHz is analyzed when a pulse repetition frequency (PRF) of 30 kHz is used by the system. There are many methods of finding the turbulent flow pattern of the right atrium including, but not limited to, neural networks, wavelets, fuzzy logic, expert systems, pattern recognition, and artificial intelligence.

In one embodiment of the turbulent flow analysis, the frequency content of the acoustic signal is monitored over time. One method is to use a Fourier Transform or a power spectral analysis of the incoming signal using overlapping or non-overlapping windows. These windows may be filtered using a variety of methods including, but limited to, Hamming, Hanning, rectangular, Gaussian, among others. After the acoustic signal is windowed, filtered, and transferred from the time domain to the frequency domain, the magnitude and phase of the frequency components of the signal are monitored over time. In the veins leading to the heart, the antegrade frequency components will be larger in magnitude than the retrograde components. If the probe enters an ancillary or undesired vessel en route toward the heart, the retrograde components will be larger than the antegrade components.

In the right atrium, the frequency components will vary between antegrade dominant to retrograde dominant as the right atrium contracts. The rapid changes from antegrade to retrograde dominated signal even though the stylet may be stationary are indicative of turbulent blood flow pattern of the right atrium. There are many methods of monitoring this rapid change. For instance, one could monitor the change of frequency components in the antegrade signal. Instead of small changes in the frequency components associated with each heart contractions as seen in the vein, the right atrium will produce large and distinctive changes in the frequency components with each heart contraction. For example, in the vein, about a 5 to 7 kHz change in the frequency components with each heart contraction is generally expected, depending on the location within the venous vasculature, while in the right atrium, about a 7 to 15 kHz change is generally expected, when using a PRF of 30 kHz. In addition, the shape of the frequency signal can be different, with the vein having a frequency component signal with a relatively smooth shape, and the right atrium having a frequency component signal with a relatively sharp and random shape. One could also use the retrograde signal for the analysis. While the stylet is in the veins, the retrograde signal will be weak or minimal. Once the transducer enters the right atrium, the magnitude of the retrograde signal will increase and will vary with each atrial contraction and respiration.

Figure 3:
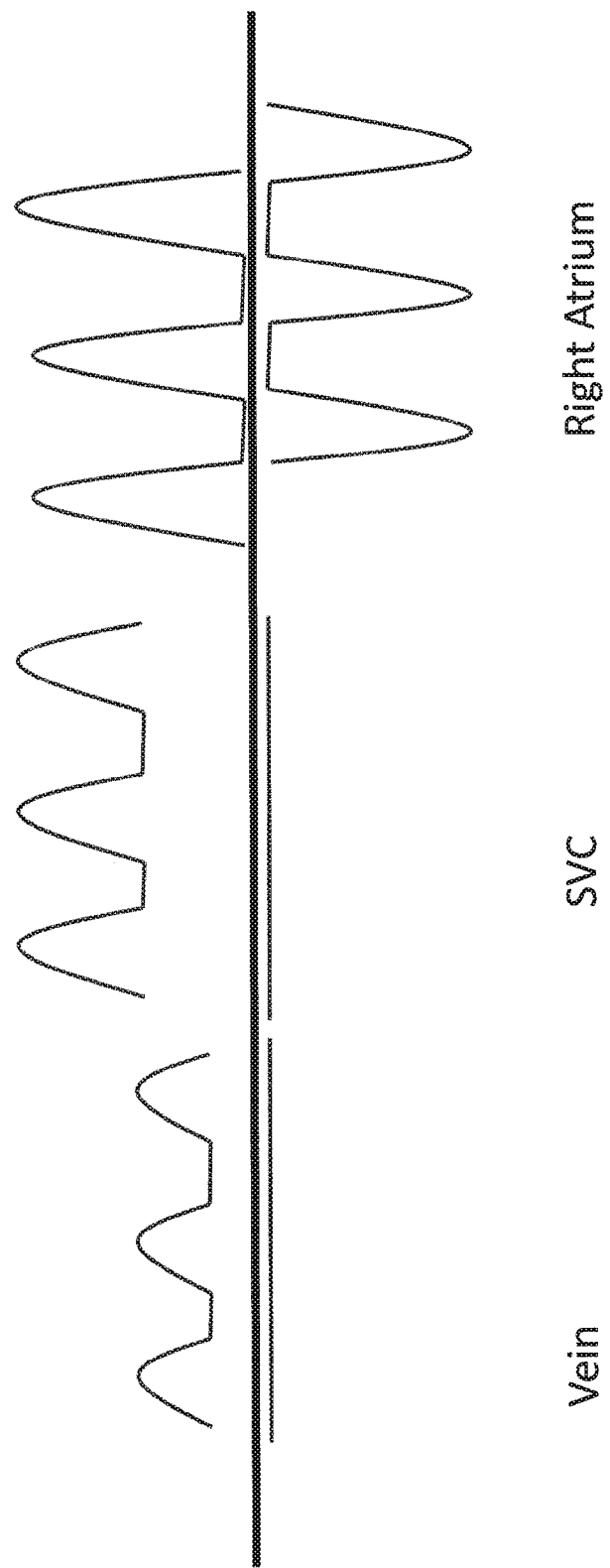
FIG. 3 illustrates how flow characteristics change between the peripheral vein, the SVC and the right atrium.

An additional embodiment of monitoring turbulent blood flow is to monitor frequency component peaks as the blood flow changes direction. When the turbulent blood flow changes direction, the frequency component will change creating a peak. The peaks and troughs (local maximums and minimums) will indicate the how often the blood flow velocity changes, the magnitude of these changes, and the timing of the changes. For example, FIG. 3 illustrates how these features change in a peripheral vein, the SVC and the right atrium. In the vein and the SVC, the flow is primarily unidirectional (antegrade), but the signal magnitude in the SVC is greater than the vein. In the right atrium, there is bidirectional flow with a large magnitude. The timing of changes in blood flow will help determine if the changes are associated with a heart contraction, respiratory rhythm, or moving of the catheter tip. In some embodiments, the peaks and troughs can be compared with ECG measurements and data to determine whether the changes are associated with the heart rate.

Another feature of the turbulent signal could be the ratio of the antegrade power to the retrograde power signal. For example, the ratio of the spectral power of the antegrade signal to that of the retrograde signal can be used. While the transducer is in the main vein, the power of the antegrade will be dominant. If the transducer is in an ancillary vein, the signal will be retrograde dominant. If the transducer is in the right atrium, the power the acoustic will vary rapidly between antegrade and retrograde dominant. In the right atrium, if one were to average the power over one cardiac cycle, the ratio between antegrade and retrograde will be close to unity in turbulent blood flow since the both signals are present. In some embodiments, close to one can mean within 30% of unity, or within 20% of unity, or within 10% of unity. In addition, the ratio will generally be greater than one just past the CAJ, and closer to the IVC, the ratio will be generally less than one.

There may be turbulent blood flow where two veins combine (for instance where the brachiocephalic vein meets the internal jugular vein) because the two blood flow are merging in a chamber than is larger than either vein. These small sections of turbulent blood flow need to be differentiated from turbulent blood flow of the right atrium. One method to differentiate the two types of turbulent blood flow will be based on the overall power of the acoustic signal. The power of the acoustic signal in the right atrium will be much larger than the power at one the ancillary venous junctures. Another method is to measure the power of the retrograde component of the turbulent blood flow. The retrograde flow at the ancillary venous juncture which has no retrograde source will be much lower than at right atrium which has the IVC providing the retrograde source of the turbulent blood flow.

Another embodiment of the analyzing the acoustic signal for turbulent blood flow will be to create Mel-frequency cepstrum (MFC) of the acoustic signal. MFC is a presentation of the short-term power spectrum of an acoustic signal based on a linear cosine transform of a log power spectrum on a nonlinear Mel scale of frequency. The coefficients of the MFC are the acoustic characteristics of the acoustic signal for the short time period. These MFC coefficients (MFCC) are compared to a database of previously recorded MFCC from turbulent and non-turbulent blood flow. At each time step, the MFCC of the sampled signal will be compared to the stored MFCC such that a scoring of the match can be made. This comparison step could be done by a variety of means including, but not limited to, support vector machines, Gaussian Mixture Models, Mahalanobis Distance, and neural networks. The scores from each stored MFCC are then compared against each other and over time to determine the most probable blood flow pattern. This comparison can be done via a variety of methods including hidden Markov chains, K means, nearest neighbor, codebook indexing, AdaBoost, Bayesian model, and neural networks. In one embodiment, the hidden Markov chain will analyze the series of scores from each stored MFCC. Based on the model parameter, the model will then output the state (blood flow pattern) of the system.

Besides using MFC to characterize, one skilled in the art could also use different acoustic scaling such as Bark scale, Fletcher-Munson curves, or any other audiometric weighting curves. Other feature extractions of the acoustic signal are linear predictor coefficients and frequency domain enveloping among others. These techniques can be used to generate coefficients that can be compared to a database of coefficients values from known locations in the venous vasculature and circulatory system.

In some embodiments, another feature that can be extracted is the instantaneous respiratory rate of the patient. The inserted catheter can move with each respiratory cycle creating a low frequency modulation of the acoustic and ECG signals. The movement may confound the analysis of the acoustic and ECG signal and especially the turbulent flow analysis. The movement of the catheter can change the position of the ultrasound transducer within the right atrium. Depending of the location of the transducer, the magnitude of the antegrade, retrograde, and turbulence will change. For instance, if the transducer is in the right atrium near the SVC, then the turbulent signal will be antegrade dominant. If the transducer is in the right atrium near the IVC, then the turbulent signal will be retrograde dominant. The transducer movement caused by the respiratory cycle could move the transducer from the bottom of the SVC to the top of the IVC causing the signal to oscillate from an antegrade dominant to retrograde dominant turbulent signal.

In some embodiments, one method of monitoring respiration is to monitor and analyze the R wave portion of the ECG. The amplitude of the R wave increases with expiration and the amplitude decreases with inspiration. The R-R interval also increases with expiration and decreases with inspiration. Based on these two features, the respiratory cycle can be determined (see Bowers, Murray, & Langley, 2008, which is hereby incorporated by reference in its entirety). The respiratory cycle components of the acoustic and ECG signal may be removed before the features are sent to the processor to increase the accuracy of the features. In some embodiments, the acoustic and ECG signals can be monitored and analyzed during a predetermined portion of the respiratory cycle, such as the beginning of inspiration, the beginning of expiration, the end of inspiration, the end of expiration, the middle of inspiration, and/or the middle of expiration.

In other embodiments, respiration can be monitored using an accelerometer that measures the periodic movement of a patient's chest during respiration.

In some embodiments, once the features are measured during the pre-processing stage, the features are passed into the processor to determine the output, such as stylet location for example, that will be displayed to the user. As discuss above, the features can be inputted into their respective membership functions for each states 0, 1, 2, and 3. However, the right atrium, or another anatomical location, can be an additional state or states: state 4 and so on. The final score of each "class" is a weighted sum of the output scores from all the parameter membership functions (i.e. membership functions for D1, D2, D3, and E1).

The weighted sum of the output scores from all the feature membership functions for one class is as follows.

$$S_R = \sum_n w_R(n) \cdot S_R(n)$$

The above equation represents one of the output scores for red (state 3). "n" refers to the number of parameter features. Generally, the scores for each of the classes corresponding to the different states increase and decrease in likelihood with the membership function.

Final scores are output by the processor. The processor then determines the state of navigation based on the highest score. The state with highest score is displayed to the user. In the above example, if $S_R$ is the highest score with state 3, the processor outputs a result related to State 3. In another example, if the highest score corresponds to state 4, the processor provides an result to the output device to display right atrium.

In some embodiments, the above function does not take into account the output of previous states. For instance, the state at time $t_{n-1}$ does not influence probability of obtaining any state at time $t_n$. Of states 0 through 3, only state 2 provides an exact location to the user. Once state 2 is achieved, the user stops moving the catheter since the catheter is in the ideal or target location. The other 3 states only provide general directions (move forward, pull back, etc.). Given that the previous states do not provide information on how close the catheter tip is to the CAJ point, the current state is not dependent on the previous states.

However, the right atrium is an exact location. Once the catheter reaches the right atrium, it has only 5 places to go: IVC, right ventricle, coronary sinus, CAJ, or stay in the right atrium. Giving the limited number of locations to go, in some embodiments, the system can gate the rules the processor uses based on location within the right atrium. The processor can use the general formulation used above. If the state ever changes to state 4 (right atrium), the processor can change the weighting on the formula or use a different formula all together.

Once the system determines that the catheter tip is located in the right atrium, the formula can change from the original formula (below) to a new formula such that the weights are different for the same state.

$$S_R = \Sigma_n w_R(n) \cdot S_R(n)$$

In the example below, the score for the State 3 (Red) can be based on a different set of weight ($w_{R_2}$) instead of the original weights ($w_R$). The formula can also use a different set of features to calculate the score. In the example below, the features in the original ($S_R$) is changed to $S_{R_2}$.

$$S_R = \Sigma_n w_{R_2}(n) \cdot S_{R_2}(n)$$

In some embodiments, after determining location within the right atrium, the new processor formula can be solely based presence or absence of turbulent blood flow pattern analysis. The turbulent blood flow will only decrease if the catheter is moved into the IVC, the CAJ, or the ventricle. The IVC will be a retrograde dominant signal. The ventricle will be highly pulsatile blood flow associated with the R wave. The CAJ will be antegrade dominant and represent State 2. Since the right atrium indicator can tell the user to slowly withdraw the catheter, the most likely state achieved after State 4 will be State 2. Therefore, the processor may be weighted to take into account that State 2 will be a highly probable state once the user leaves State 4. For example, $w_{R_2}$ can be increased after achieving State 4, to reflect the high probability that State 2 will be achieved next.

Other embodiments of the gating of the processor formula can be used once the location of the catheter tip is determined. For instance, if the processor can determine the location of the SVC, then the processor knows any turbulent signals found will be associated with the right atrium since the stylet tip has already passed all ancillary venous junctures. Therefore, the weighting and/or features of the state functions can be changed to reflect this information.

Figure 2:
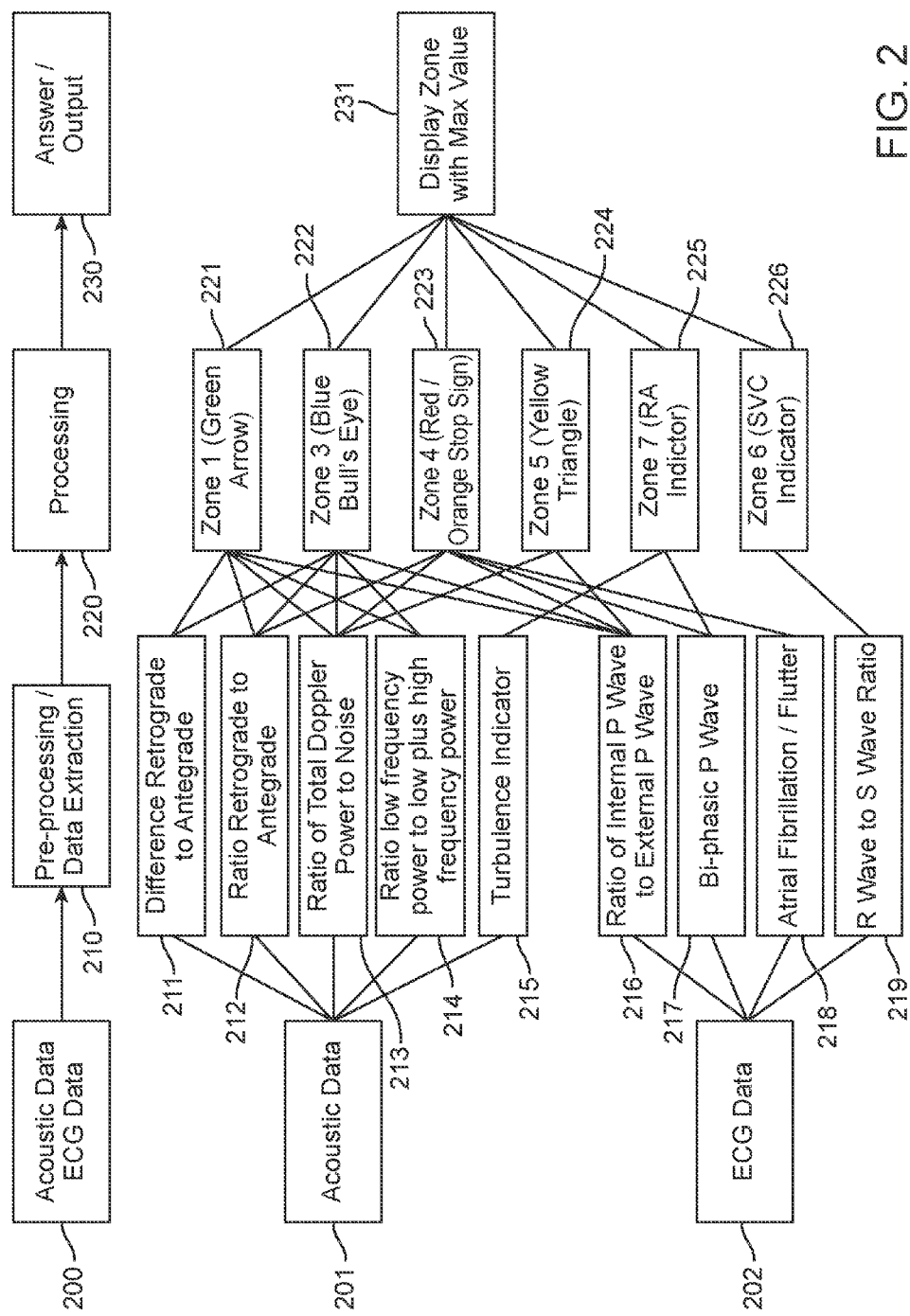
FIG. 2 is a flow chart of the embodiment illustrated by FIG. 1 further illustrating the various features that can be extracted from the sensor data and how the features can be used in the navigation procedure.

FIGS. 1 and 2 are flow charts illustrating embodiments of the methods described above. In step 100, acoustic data and ECG data are acquired by recording signals from the ultrasound transducer and ECG sensor of the probe. Next, in step 110, the recorded data undergoes pre-processing and feature extraction before being passed to the algorithms for further processing. During pre-processing and data extraction, specific values of a variety of features are identified and provided as inputs to the algorithm. Pre-processing can include time to frequency conversion of the acoustic signal, filtering and de-noising as further described above. Data extraction includes extracting a variety of features from the raw data, including the power level, the QRS complex, the P, Q, R, S, and T wave, retrograde or antegrade flow dominance, frequency content, frequency content morphology, and other Doppler and/or ECG features, such as the area under the curve, minimums, maximums, derivatives, and integrals.

For example, FIG. 2 shows that features that can be extracted from acoustic data 201 include the difference between retrograde flow to antegrade flow 211, the ratio of retrograde flow to antegrade flow 212, the ratio of total Doppler Power to Noise 213, the ratio of low frequency power to low plus high frequency power 214 (total frequency component), and turbulence indicators 215. Features that can be extracted from ECG data 202 include the ratio of internal P Wave to external P Wave 216 (internal refers to P Wave measured from intravascular ECG sensor located on the stylet while external P Wave refers to P Wave measured from ECG electrodes located on the skin), bi-phasic P wave characteristics 217, atrial fibrillation/flutter 218, and R Wave to S Wave ratio 219.

Returning to FIG. 1, after the data has be pre-processed and the features have be extracted, the pre-processing data and extracted features are passed to the algorithms for further processing 120. The algorithms can include membership functions and weightings that are used to determine zones or states of the device as described above. The results of the processing 120 can be output to the user 130 using a visual indicator or display or audio indicator.

FIG. 2 illustrates examples of which features can be used to determine the values of the membership functions for the plurality of zones or states. For example, Zone 1 221, which can be represented by a green indicator such as an arrow, indicates to the user to continue advancing the device. The features that can be included in the membership function for Zone 1 include difference in retrograde to antegrade flow 211, ratio of retrograde to antegrade flow 212, ratio of total Doppler power to noise 213, ratio of low frequency power to low plus high frequency power 214, and ratio of internal P Wave to external P Wave 216. Zone 3 222, which can be represented by a blue indicator such as a bull's eye, indicates that the target location has been reached. The features that can be included in the membership function for Zone 3 include difference in retrograde to antegrade flow 211, ratio of retrograde to antegrade flow 212, ratio of total Doppler power to noise 213, ratio of low frequency power to low plus high frequency power 214, and ratio of internal P Wave to external P Wave 216. Zone 4 223, which can be represented by a red or orange indicator such as a stop sign, indicates to the user stop and withdraw or retract the device. The features that can be included in the membership function for Zone 4 include ratio of retrograde to antegrade flow 212, ratio of total Doppler power to noise 213, bi-phasic P wave characteristics 217, and atrial fibrillation/flutter 218. Zone 5 224, which can be represented by a yellow indicator such as a triangle, indicates to the user to stop and wait. The features that can be included in the membership function for Zone 5 include ratio of total Doppler power to noise 213 and ratio of internal P Wave to external P Wave 216. Zone 7 225, which can be a right atrium indicator, indicates that the right atrium has been reached. The features that can be included in the membership function for Zone 7 include a turbulence indicator 215 and bi-phasic P wave characteristics 217. Zone 6 226, which can be a SVC indicator, indicates that the SVC has been reached. A feature that can be included in the membership function for Zone 6 includes R Wave to S Wave ratio 219. After the values of the membership functions are determined, the zone with the highest value can be selected and outputted to the user 231 as described above.

CAJ and/or RA Turbulence Blood Flow Pattern Detection

Some embodiments of the present invention are based on the understanding that each location of the major venous vasculature from the peripheral arm vein or another peripheral vein to the heart can be identified by specific blood flow patterns quantified by ultrasound Doppler and by specific ECG features. The direction of the catheter's navigation can be determined by relative spectral power analysis (antegrade versus retrograde) of blood flow direction measured by the Doppler sensor, and by monitoring and/or measuring the change of the major ECG components.

Figure 4:
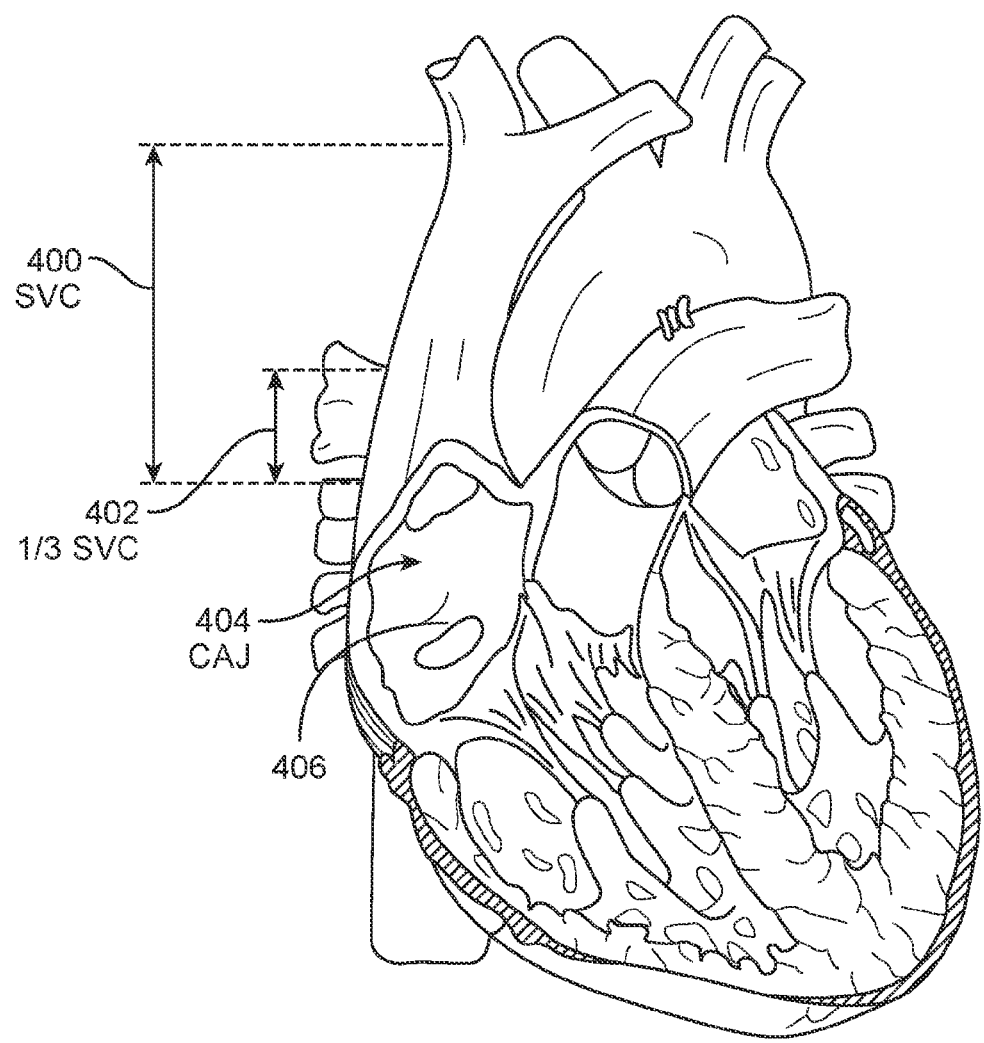
FIG. 4 is shows the anatomy of the superior vena cava (SVC) and cavoatrial junction (CAJ)

For example, in the case of a CVC or PICC line, by real-time monitoring of the direction and speed of blood flow in the venous system, a user can estimate the catheter tip location and guide the CVC or PICC to the ideal or target location, such as the ⅓ lower SVC to CAJ. FIG. 4 illustrates the anatomical location of the CAJ 404, which is located between the SVC 400 and RA 406.

Embodiments of the present invention identify the specific blood flow profile at the CAJ. One aspect of the present invention is based on the principle that certain locations in the vasculature can be identified by specific blood flow patterns. For example, the blood flow pattern in the CAJ area is multi-directional pulsatile with a high degree of turbulence. Embodiments of the present invention are intended to detect the specific (turbulent) blood flow pattern at the CAJ area using an ultrasound Doppler sensor.

Embodiments of the present invention are based on the new methods described herein in combination with non-image ultrasound Doppler blood flow pattern recognitions algorithm and ECG morphology change detection, which is further described above and in U.S. patent application Ser. No. 13/292,010, now U.S. Pat. No. 9,119,551, to guide and place the catheter in the optimal or target location. For the accurate placement of a CVC or PICC line, characterization of venous blood flow along the venous vasculature path is of importance, e.g., from the cephalic/brachial/basilic veins to the subclavian and then into the SVC along with CAJ, jugular vein, and inferior vena cava regions. In general, the mean blood velocities are slower in the veins as compared to arteries and the heart chambers. In addition, venous blood flow is weak pulsatile with low peak velocities.

Figures 5A, 5B, 5C, 5D:
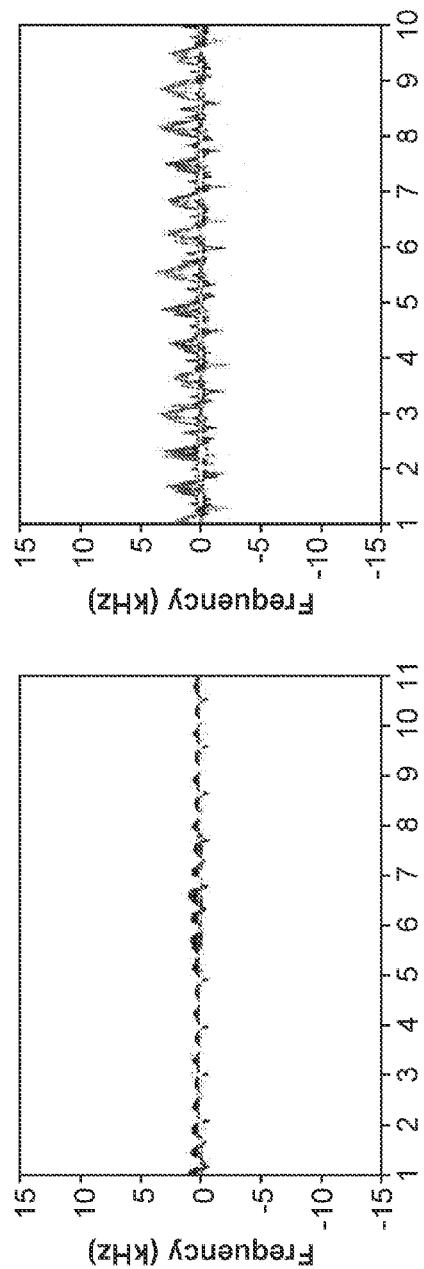
FIGS. 5A-F show exemplary Doppler signals on the time-frequency domain at various locations within the vasculature.
Figure 5F:
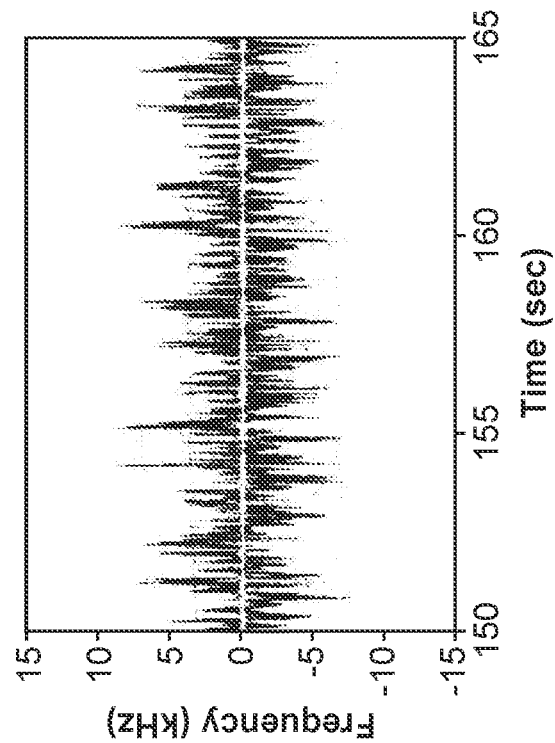
Figure 5E:
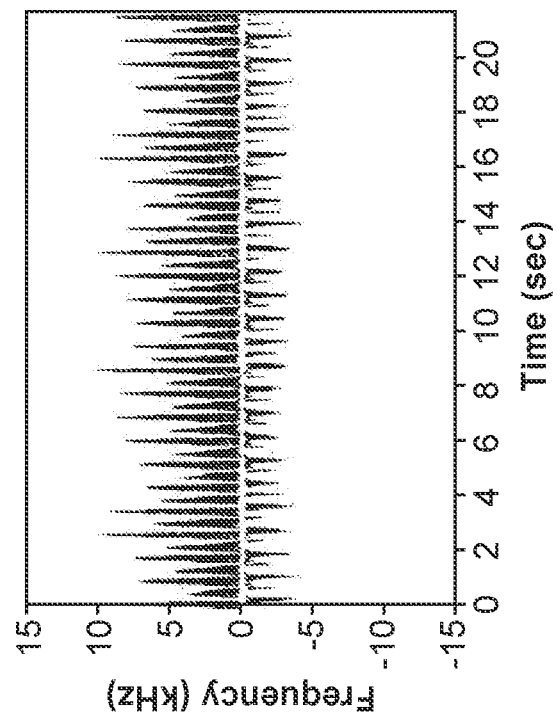

In the upper extremity venous (cephalic, brachial, subclavian and basilic), the blood flow is generally weak pulsatile, as illustrated in FIGS. 5A-D. In FIGS. 5A-5F, the x-axis represents time in seconds and the y-axis represents the frequency in kHz. In the SVC, the blood flow is generally unidirectional pulsatile, as illustrated in FIG. 5E. In the CAJ and RA, the blood flow is generally multi-directional pulsatile with a high degree of turbulence, as illustrated in FIG. 5F and FIGS. 9A and 9B. FIG. 9A illustrates the multi-directional blood flow pattern and/or turbulent blood flow pattern caused by the blood flow from the SVC and IVC, while FIG. 9B illustrates the contribution from movement of the RA walls. The weak pulsatile pattern of the upper extremity venous flow lightly follows the pulsatile pattern of the heartbeat. Since the venous weak pulsatile pattern differs from the multi-directional pulsatile pattern in the CAJ area and the RA, the pattern analysis algorithm detects these significant pattern differences of the different locations of interest, and helps the user place an endovascular catheter in the ideal or target location. Various aspects of the invention relate to ultrasound Doppler data processing algorithms that can accurately characterize the direction and velocity of blood flow at the catheter location and guide the catheter to the optimal or target location.

In some embodiments, a pre-processor calculates the level of background noise from the Doppler signal in the initial catheter insertion session. The background noise can be calculated by adding the first 7 seconds of Doppler data within the pre-defined high frequency bandwidth (i.e., 11.43 kHz to 13.42 kHz or about 11 kHz to 14 kHz). In the beginning of the procedure while in the peripheral vasculature such as the brachial artery, blood flow generally does not reach this high frequency bandwidth range. If the level of background noise is higher than a threshold value due to a medical procedure such as flushing a catheter, then next 7 seconds of Doppler data is studied. Afterwards, the level of background noise for each frequency point is calculated. This value is then subtracted from the entire set of frequency points to increase the signal-noise ratio.

In some embodiments, a pre-processor can extract physiological parameter information from the ultrasound Doppler data. Exemplary physiological parameters described here include: total frequency power, low frequency band power, medium frequency band power, high frequency band power, very high frequency band power, ratio between each frequency power and total frequency power. In addition, the upper envelope (maximum) of the antegrade blood flow and the lower envelope (minimum) of the retrograde blood flow can be constructed from the ultrasound Doppler signal. The preprocessor extracts information from the envelope signal. Exemplary information include: maximum height envelope, total area under the envelope line, mean envelope value, length (duration) of envelope in each beat, percentile area of the specific bandwidth, and ratio between above parameters.

The parameters listed above are used as input data in the processing algorithms, which can be based on artificial intelligence, for example Neuro-Fuzzy logic. The algorithms can also be based on, for example, expert systems, neural networks and genetic algorithms. The processor contains a set of processing rules including membership functions and Fuzzy rules to process in vivo intravascular and external ECG and non-imaging ultrasound Doppler signals to determine SVC area and the probable location of the intravascular catheter tip.

The processor with a set of processing rules can evaluate a blood flow pattern and a frequency power within a specific bandwidth of the ultrasound Doppler signal on a beat-to-beat base. In some embodiments, the blood flow patterns can be classified as the following types: antegrade blood flow Doppler signal is dominant over retrograde blood flow Doppler signal (Type 1), both antegrade flow Doppler signal and retrograde flow Doppler signal show well balanced waveform or turbulence patterns (Type 2), retrograde blood flow Doppler signal is dominant over antegrade flow Doppler signal (Type 3), and both antegrade and retrograde flow Doppler signals are concentrated in the low frequency band (Type 4). In some embodiments, the location of interest is the lower part of CAJ area and the upper part of the atrium. This location is characterized by distinct turbulent blood flow patterns (Type 2). The present analysis algorithm detects the presence of turbulent blood flow patterns in and around the CAJ area by analyzing one or more of the following Doppler features:
1) Maximum amplitude>=2.3 kHz (both antegrade and retrograde flow)
2) 0.6<=Ratio (maximum amplitude of Antegrade/Retrograde flow)<=1.3
3) Percentage of Antegrade & Retrograde Doppler signal at 0.2930 kHz vs total possible signal>=50
4) Percentage of Antegrade & Retrograde Doppler signal at 40% max kHz vs at 0.2930 kHz>=30
5) 0.6<=Ratio (total Antegrade area/total Retrograde area) <=2.5
6) Area at Very high frequency (6.9727 kHz to 14.6484 kHz)
7) Antegrade<=10 & Retrograde<=5
8) Retrograde signal at maximum antegrade Doppler point In addition, in some embodiments, the beat-to-beat CAJ area can be estimated or determined with an analysis of changes of the ECG waveform due to the atrium and ventricular activities during the cardiac cycle. As illustrated in FIGS. 10A and 10B which illustrate exemplary ECG waveforms for two different patients, these ECG features include, for example, (1) P wave amplitude, (2) area under the P waveform, and (3) interrelationships of the atrium and ventricular parameters including, for example, (4) QRS complex amplitude, (5) area under the QRS waveform, (6) T wave amplitude, (7) area under the T wave waveform, and (8) ratios or differences between various components of the ECG waveform including, for example, P versus QRS (amplitude and/or area under the waveforms), P versus T (amplitude and/or area under the waveforms), T versus QRS (amplitude and/or area under the waveforms), and the like.

For example, an analysis of FIGS. 10A and 10B illustrates that both the T wave amplitude and the P wave amplitude increases between the ECG waveform measured in the peripheral vein and the ECG waveform measured in the CM. In general, the system and method identifies differences between the ECG waveforms in the peripheral vein and the location of interest, such as the SVC, CAJ or other location, which are consistently found among a large population of patients. These consistently identified relationships can be incorporated in the features, parameters, constants and algorithms described herein to help locate the stylet.

In some embodiments, the ratio of the beat-to-beat feature value to an initial feature value is compared with a threshold feature value, where the beat-to-beat feature value refers to the present or current feature value during the navigation procedure, the initial feature value refers to the feature value measured after insertion of the stylet or during initial calibration, and the threshold value is a value determined from a database of patient data such that when the ratio exceeds the threshold, it is likely that the stylet is in the CAJ and/or RA or some other target location.

In addition, in some embodiments, the values of the initial feature value and/or the value of the threshold feature value can be constrained to a predetermined range. In some embodiments, the threshold feature value can be a predetermined constant. For example, one or more of a lower bound and a higher bound can be set for the initial feature value and/or the threshold feature value. For example, the above relationships can be expressed in equations such as the following, which uses the P wave amplitude as an example:

$$P_{init} = \begin{cases} A_1 & P_{init} \leq A_1 \\ P_{init} & A_1 < P_{init} < B_1 \\ B_1 & QRS_{init} \geq B_1 \end{cases}$$

$$P_{Thres} = \begin{cases} \alpha_1 & P_{init} \leq A_1 \\ \alpha_2 & A_1 < P_{init} < B_1 \\ \alpha_3 & P_{init} \geq B_1 \end{cases}$$

$$\text{If } \frac{P_{Beat\text{-}to\text{-}beat}}{P_{init}} \geq P_{Thres}, \text{ show } CAJ \text{ sign}$$

These equations specify that the initial P value has a value between $A_1$ and $B_1$, which can be constants with predetermined values. This means that when the initial P value is being determined, during for example the calibration procedure, and the measured P value is less than $A_1$, then the initial P value is assigned a value of $A_1$. If the measured P value is between $A_1$ and $B_1$, the initial P value is assigned a value of the measured P value, and if the P value is greater than $B_1$, then the initial P value is set at $B_1$.

Figure 11:
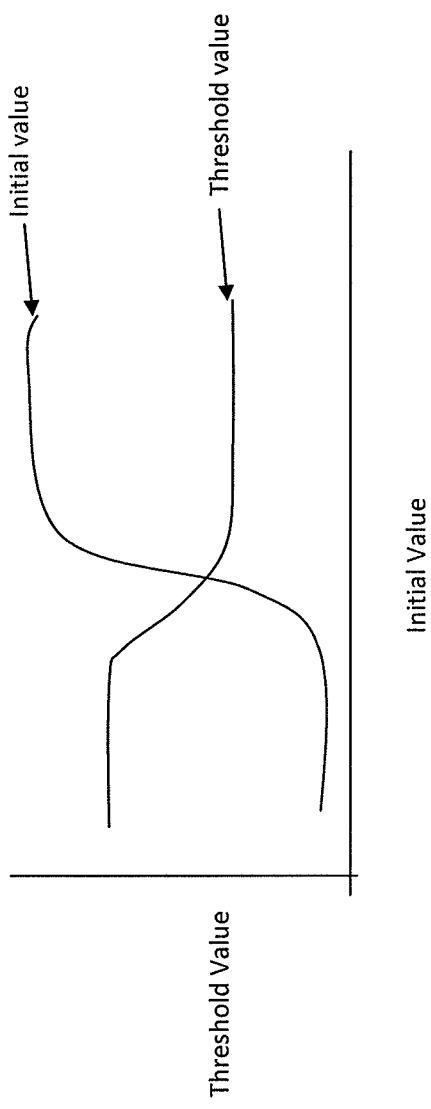
FIG. 11 illustrates an embodiment of the relationship between the initial feature value and the threshold feature value.

In some embodiments, instead of or in addition to using the comparison between the ratio and the threshold, a delta feature value can be determined, where the delta feature value is equal to a product between a sigmoid weighting factor and a value that is a function of the beat-to-beat feature value and optionally other variables, parameters or constants, such as the upper threshold for example, which can also depend on a variety of factors, such as the initial feature value, the signal strength or quality, and the like. The delta feature value can be compared with the threshold feature value, where the threshold feature value is selected such that when the delta feature value exceeds the threshold feature value, it is likely that the stylet is in the CAJ or some other target location. The value of the sigmoid weighting factor can depend on, i.e. can be a function of, the initial feature value and/or other variables. Similarly, the threshold feature value can depend on, i.e. can be a function of, the initial feature value and/or other variables as illustrated in FIG. 11. The following equations represent these relationships:

$$F_\Delta = Weight_{sigmoid} \times f(X, F_{Beat-to-beat})$$

Figure 6A:
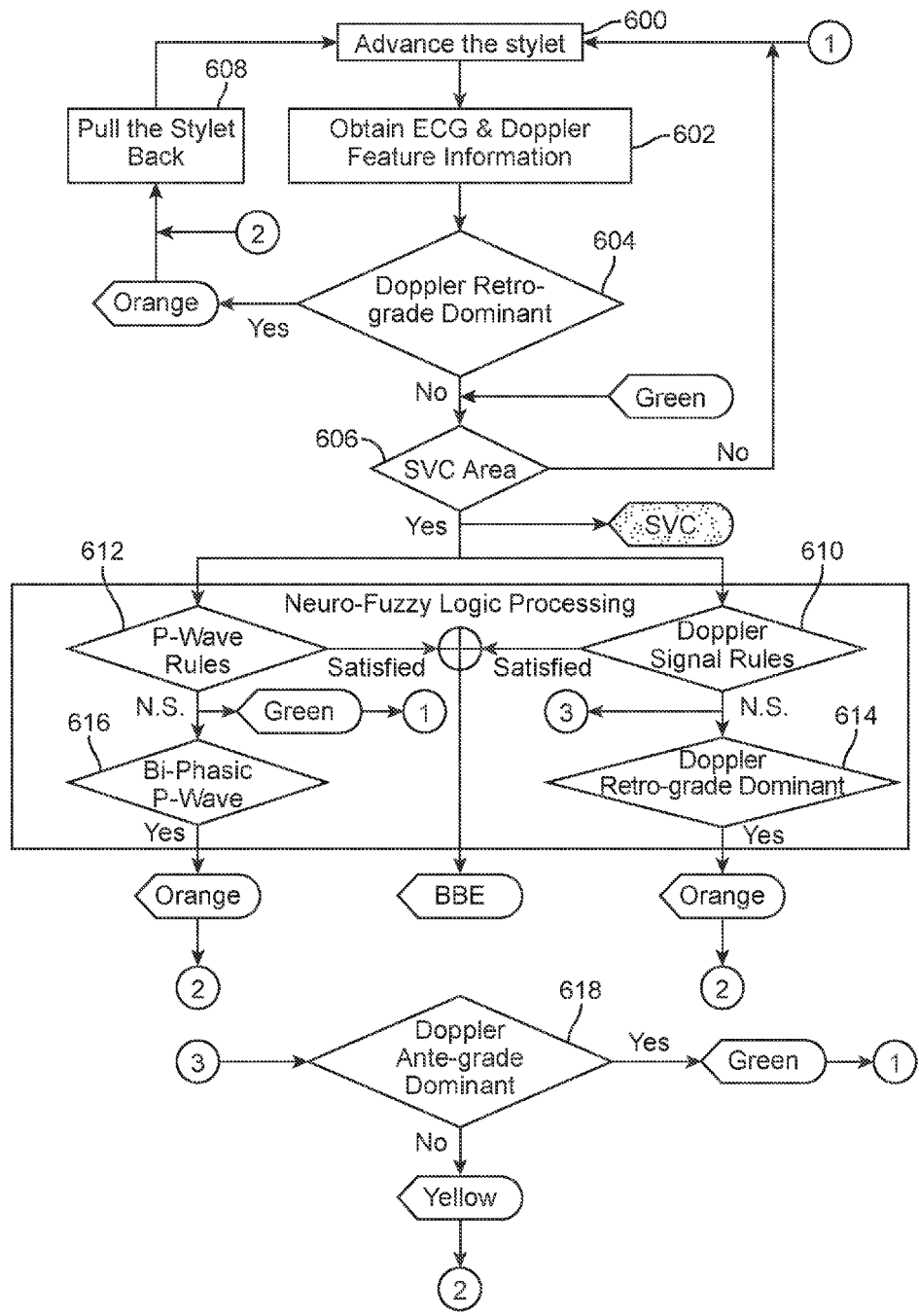
FIG. 6A shows a flow chart describing generally an embodiment of the navigation process.
Figure 6B:
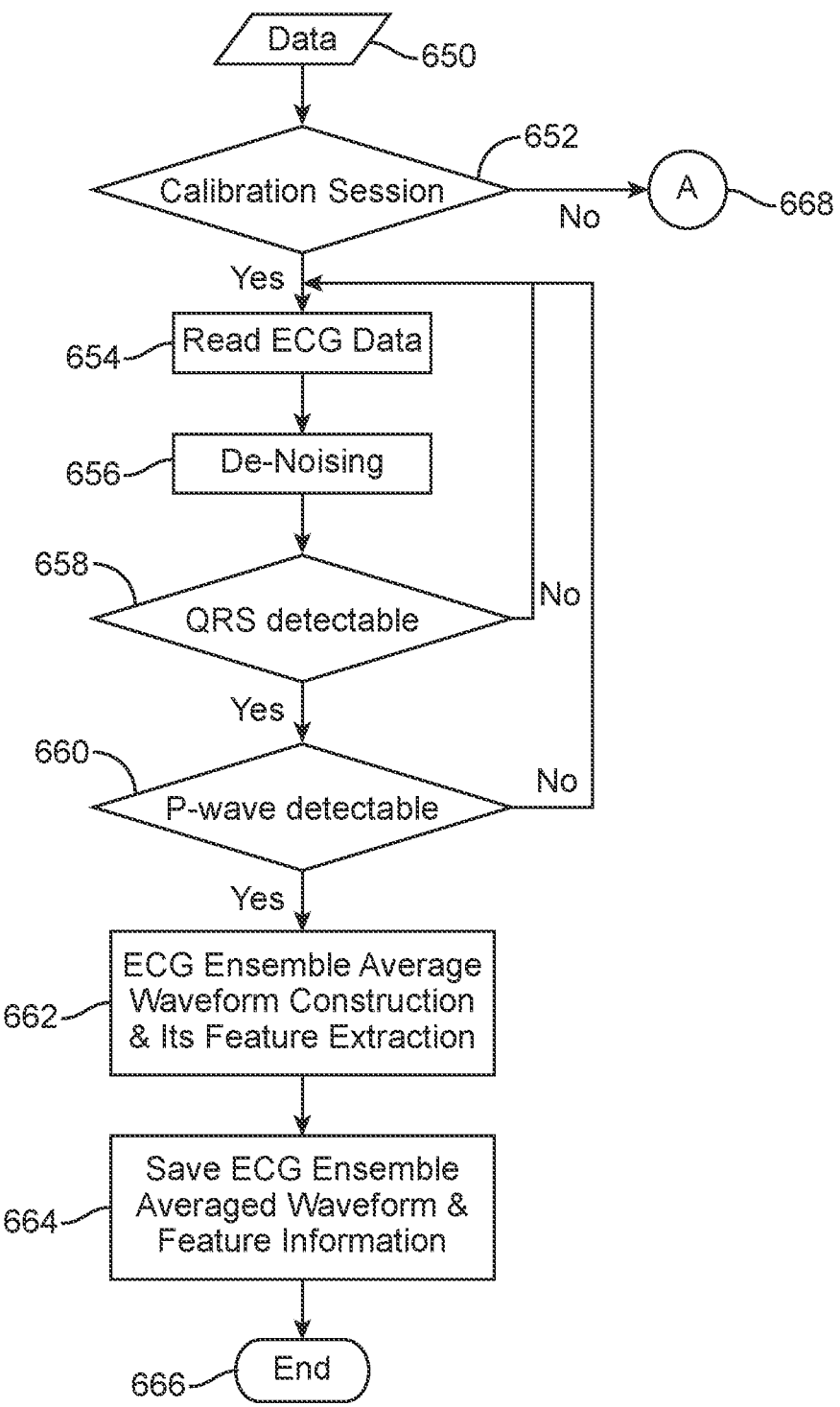
FIG. 6B shows a flow chart of an embodiment of the calibration process.

If $F_\Delta \geq F_{Thres}$, high probability to show CAJ or blue bulls eye sign Overall System and Method With the system algorithm, which can be based on Neuro-Fuzzy logic, extracted features are processed and a weighing factor is assigned to each feature based on the evaluation of ECG, acoustic and Doppler signals. In some embodiments, a subset of the above features, such as one, two or more features, can be used for the analysis. For, example, one embodiment of the algorithm The preprocessor conducts high-level feature extraction processing of the data. The processor implements the algorithms to make the final decision of the catheter location. During the catheter insertion with the stylet, the guidance system provides four different location indicators: a green arrow (move forward), the blue bull's eye (right location), a red or orange indicator (stop and pull back), and yellow triangle (no decision due to the lack of data). These location indicators guide the clinical operator to place the catheter in the optimal location. FIGS. 6A and 6B illustrate simplified general steps for catheter guidance according to various embodiments.

Additionally, the location of the catheter tip may provide a gating function for the processor such as changing the weights, parameters, features and formulas of the algorithms based on the current location of the catheter tip to increase the accuracy of the placing the catheter tip in the ideal or desired location. For example, if the processor can determine the location of the SVC, then the processor knows any turbulent signals found will be associated with the right atrium since the stylet tip has already passed all ancillary venous junctures. Therefore, the weighting and/or features of the state functions can be changed to reflect this information. Additionally, the features from the acoustic signals and the features from the Doppler signals can be used to identify whether the multidirectional flow or turbulence detected by the system and method is turbulence at the junction of two veins or turbulence in the RA/CAJ. One feature, as described above, which can be used to make this distinction is the overall power of the acoustic signal, which will be larger in the RA/CAJ than at the junction of two veins. Therefore, a state representing the RA/CAJ can weigh the overall power of the acoustic signal more heavily than a state representing the junction of the two veins.

As illustrated in FIG. 6A, the method begins after the insertion of a stylet, catheter or other device into a peripheral vein of the patient with step 600, where the stylet is advanced. Then, at step 602, ECG and Doppler feature information is obtained. Using this information, at step 604 the system determines using the Doppler data whether retrograde flow is dominant. If retrograde flow is dominant, the system activates the red/orange indicator which prompts the user to go to step 608 and pull the stylet back and then start over at step 600. If, however, flow is not retrograde dominant, the system activates the green indicator, the stylet is advanced, and the system checks whether the SVC area has been reached at step 606. If the SVC has not been reached, the green indicator is activated and the stylet is advanced. If however the system determines that the SVC area has been reached, the system proceeds to evaluate the Doppler signal rules at step 610 and P wave rules at step 612. If both sets of rules are satisfied, then the target location (i.e., ⅓ lower SVC) has been reached and the blue bull's eye indicator can be activated.

If however, the Doppler signal rules have not been satisfied, the system determines whether the flow is retrograde dominant or antegrade dominant using the Doppler data. If the flow is retrograde dominant 614, the red/orange indicator is activated, which instructs the user to pull the stylet back, which sends the process back to step 600. If the flow is clearly antegrade dominant, then the green indicator is activated, which instructs the user to advance the stylet, sending the process back to step 600. If the flow is not clearly antegrade dominant, the yellow indicator is activated, which instructs the user the wait and sends the process to step 608.

If however, the P wave rules are not satisfied, the system determines whether the P wave is biphasic 616. If the P wave is biphasic, the red/orange indicator is activated, which instructs the user to stop and pull back, and the process is directed to step 608. If the P wave is not biphasic, then the green indicator is activated, which instructs the user to advance the stylet and returns the process to step 600.

FIG. 6B illustrates a calibration procedure. Starting at step 650, ECG data is obtained. Then at step 652 the system determines whether the ECG data was collected as part of a calibration or not. If not, the ECG data is sent for pre-processing and processing 668 as illustrated in FIG. 8. If a calibration session is indicated, the process proceeds to step 654 where the ECG data is read, then de-noised at step 656, and sent to step 658 to determine whether the QRS complex is detectable. If not, the process is sent back to step 654 and the next ECG data is read. If the QRS complex is detectable, the process proceeds to step 660 where the system attempts to detect the P wave. If the P wave is not detectable, the process is sent back to step 654. If the P wave is detectable, the process proceeds to step 662 where the system constructs an ECG ensemble average waveform and extracts the ECG features. Then the process proceeds to step 664, where the ECG ensemble average waveform and extracted features are saved, which ends the calibration session 666.

Figure 7:
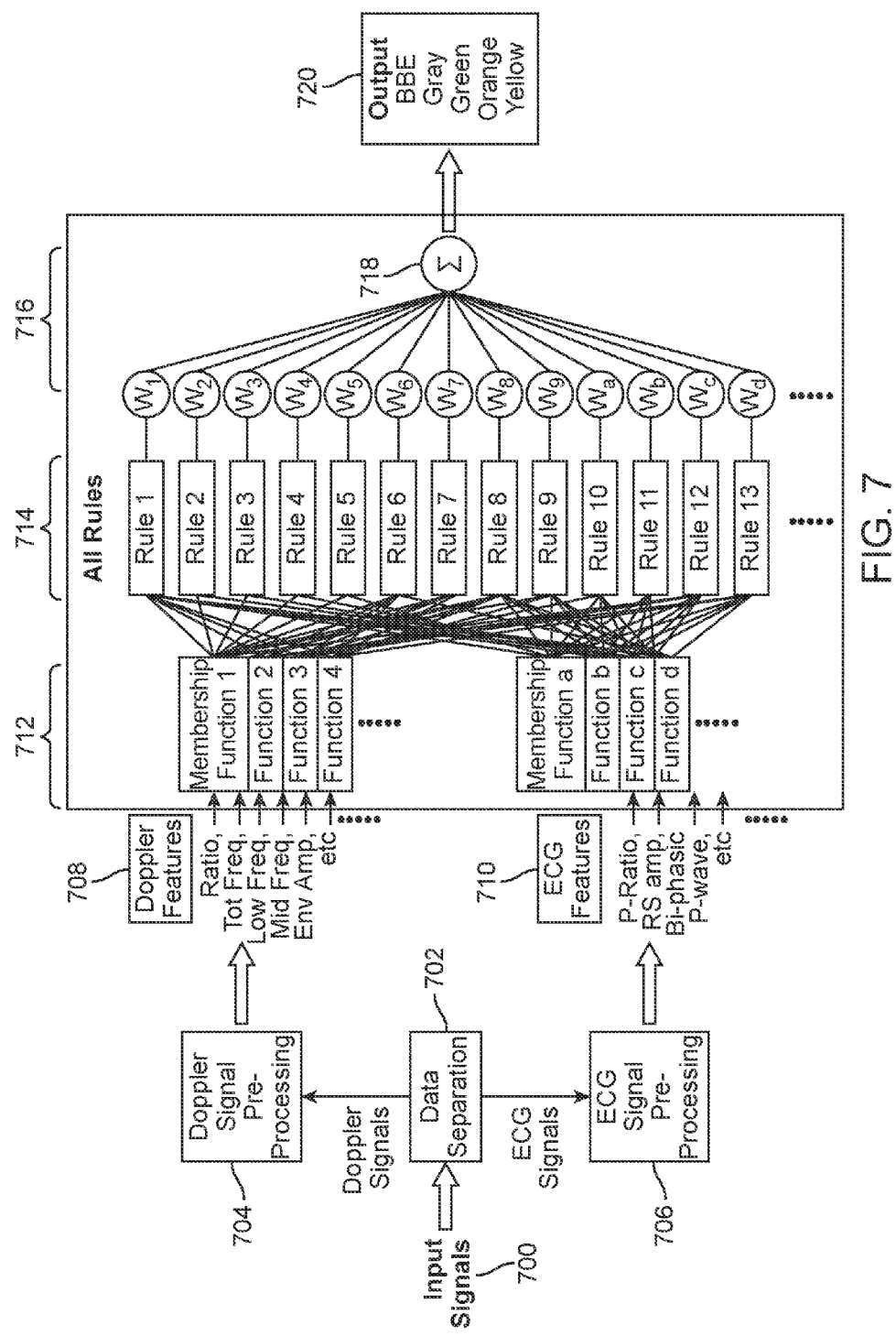
FIG. 7 shows an embodiment of the processing of data.

FIG. 7 illustrates a diagram of the logic process, which can be Neuro-Fuzzy, of the collected ECG and Doppler data, which are further described herein and in U.S. application Ser. No. 13/292,010. As shown in FIG. 7, in some embodiments, input signals 700 undergo data separation 702 into Doppler signals, which undergo Doppler signal pre-processing 704, and ECG signals, which undergo ECG signal pre-processing 706. From the Doppler signals, Doppler features are extracted 708 and from the ECG signals, ECG features are extracted 710. The extracted features are sent to membership functions 712 which are incorporated into a plurality of rules 714. Each rule is given a weighting factor 716 which can be state dependent (i.e., state 1 (green), state 2 (red/orange), state 3 (yellow), state 4 (blue), etc.). Each state can be a function of the membership functions, rules and weights 718. The state function with the highest score can be output to the user 720.

In various embodiments, both ECG and Doppler based processing for guiding and positioning of the stylet include the following operations which are illustrated in FIG. 8:

If it is the Calibration Session (FIG. 6B):
1. Get intravascular and external ECG signal, remove noise signal and
2. Detect P-wave and QRS complex,
3. Generate ECG ensemble average waveform;

If it is the PICC Navigation Session (FIG. 8):
1. Get intravascular and external ECG signal,
2. Remove noise signal from the ECG signals,
3. Detect QRS complex,
4. Calculate magnitude of QRS complex,
5. Detect P-wave,
6. Calculate magnitude and time location of the P-wave,
7. Calculate the ratio of intravascular QRS complex magnitude to external QRS complex magnitude,
8. Calculate the ratio of intravascular P-wave magnitude to external P-wave magnitude,
9. Detect the biphasic P-wave and send out a flag (internal software flag),
10. Get antegrade and retrograde blood flow Doppler data,
11. Apply filters on the Doppler data,
12. Calculate frequency spectrum of Doppler data,
13. Display time-frequency spectrum data,
14. Construct the envelop curve of the spectrum data,
15. Extract Doppler features,
16. Calculate the membership functions for the Doppler signal features and ECG signal features,
17. Assign weight to each features,
18. Calculate the final score for each possible sign,
Display sign with the highest score in each cardiac cycle.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiments whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for determining the location of a medical device within a body, the method comprising:
   transmitting from the medical device an acoustic signal;
   receiving with the medical device a reflected acoustic signal;
   advancing the medical device based on a first algorithm, the first algorithm including a first weighting factor and a first feature extracted from the reflected acoustic signal;
   determining a first location of the medical device based on the first algorithm; and
   moving the medical device to a second location based on a second algorithm, the second algorithm based on the determined first location and including at least one of a second weighting factor and a second feature extracted from the reflected acoustic signal.

2. The method of claim 1, further comprising detecting an ECG signal, wherein the first algorithm includes a third feature extracted from the ECG signal.

3. The method of claim 2, wherein the third feature is the R-wave of the ECG signal.

4. A method for guiding a medical device to a target location within a patient's cardiovascular system, the method comprising:
   transmitting from the medical device an acoustic signal;
   receiving with the medical device a reflected acoustic signal;
   extracting one or more features indicative of blood flow characteristics from the acoustic signal;
   determining a plurality of scores for a plurality of membership functions, each membership function comprising a series of extracted features, each extracted feature modified by a weighting factor, wherein the plurality of membership functions include at least one membership function for the target location within the cardiovascular system, at least one membership function for moving the device within the cardiovascular system, and at least one membership function for a secondary location within the cardiovascular system; and
   changing at least one weighting factor or at least one extracted feature in the series of extracted features of at least one membership function when the score of the membership function for the secondary location within the cardiovascular system is the greatest score.

5. The method of claim 4, wherein the target location is the SVC.

6. The method of claim 4, wherein the secondary location is the right atrium.

7. A system for determining the location of a medical device within a body, the system comprising:
   an elongate body having an non-imaging ultrasound transducer disposed on a distal portion of the elongate body;
   a processor configured to receive and process a reflected acoustic signal from the non-imaging ultrasound transducer; and
   memory for storing instructions, which when executed by the processor, causes the processor to:
      provide instructions to advance the elongate body based on a first algorithm, the first algorithm including a first weighting factor and a first feature extracted from the reflected acoustic signal;
      determine a first location of the elongate body based on the first algorithm; and
      provide instructions to move the elongate body to a second location based on a second algorithm, the second algorithm based on the determined first location and including at least one of a second weighting factor and a second feature extracted from the reflected acoustic signal.

* * * * *